US010751262B2

(12) United States Patent
Maurer et al.

(10) Patent No.: US 10,751,262 B2
(45) Date of Patent: Aug. 25, 2020

(54) CATIONICALLY CURING DENTAL COMPOSITION CONTAINING POLYMERIC PARTICLES AND USE THEREOF

(71) Applicant: 3M INNOVATIVE PROPERTIES COMPANY, St. Paul, MN (US)

(72) Inventors: Andreas R. Maurer, Langenneufnach (DE); Hendrik Grupp, Ammersee (DE); Joachim W. Zech, Kaufering (DE); Arne Thaler, Emmerting (DE); Kai H. Lochhaas, Neuotting (DE); Klaus Hintzer, Kastl (DE); Christoph Schulte, Windach (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 273 days.

(21) Appl. No.: 15/533,293

(22) PCT Filed: Dec. 8, 2015

(86) PCT No.: PCT/US2015/064365
§ 371 (c)(1),
(2) Date: Jun. 5, 2017

(87) PCT Pub. No.: WO2016/099987
PCT Pub. Date: Jun. 23, 2016

(65) Prior Publication Data
US 2017/0326038 A1 Nov. 16, 2017

(30) Foreign Application Priority Data

Dec. 16, 2014 (EP) .................................... 14198135

(51) Int. Cl.
*A61K 6/10* (2006.01)
*A61K 6/18* (2020.01)
*A61K 6/90* (2020.01)
*C08L 71/02* (2006.01)

(52) U.S. Cl.
CPC ................. *A61K 6/18* (2020.01); *A61K 6/90* (2020.01); *C08L 71/02* (2013.01)

(58) Field of Classification Search
None
See application file for complete search history.

(56) References Cited

U.S. PATENT DOCUMENTS

| | | |
|---|---|---|
| 3,453,242 A | 7/1969 | Schmitt |
| 3,729,313 A | 4/1973 | Smith |
| 3,741,769 A | 6/1973 | Smith |
| 3,808,006 A | 4/1974 | Smith |
| 3,926,636 A | 12/1975 | Barzynski |
| 4,167,618 A | 9/1979 | Schmitt |
| 4,250,053 A | 2/1981 | Smith |
| 4,394,403 A | 7/1983 | Smith |
| 4,657,959 A | 4/1987 | Bryan |
| 5,249,862 A | 10/1993 | Herold |
| 5,286,105 A | 2/1994 | Herold |
| 5,419,460 A | 5/1995 | Herold |
| 5,464,131 A | 11/1995 | Keller |
| 5,569,691 A | 10/1996 | Guggenberger |
| 5,624,260 A | 4/1997 | Wilcox |
| 5,750,589 A | 5/1998 | Zech |
| 5,865,803 A | 2/1999 | Major |
| 5,893,714 A | 4/1999 | Arnold |
| 5,907,002 A * | 5/1999 | Kamohara ............... A61K 6/10 106/35 |
| 5,918,772 A | 7/1999 | Keller |
| 6,043,295 A | 3/2000 | Oxman |
| 6,084,004 A | 7/2000 | Weinmann |
| 6,395,801 B1 | 5/2002 | Bissinger |
| 6,599,960 B1 | 7/2003 | Eckhardt |
| 7,625,442 B2 | 12/2009 | Engelbrecht |
| 2001/0004082 A1 | 6/2001 | Keller |
| 2003/0153726 A1 | 8/2003 | Eckhardt |
| 2004/0146713 A1 | 7/2004 | Schaub |
| 2004/0149164 A1 | 8/2004 | Eckhardt |
| 2005/0200585 A1 | 9/2005 | Igarashi |
| 2006/0069180 A1 | 3/2006 | Bublewitz |
| 2006/0106127 A1 | 5/2006 | Klettke |
| 2007/0090079 A1 | 4/2007 | Kelller |
| 2007/0172789 A1 | 7/2007 | Muller |
| 2008/0200585 A1 | 8/2008 | Klettke |
| 2009/0151983 A1 | 6/2009 | Sempliner |
| 2010/0035210 A1 | 2/2010 | Suchan |
| 2013/0101954 A1 | 4/2013 | Riedel |
| 2014/0154646 A1* | 6/2014 | Blackwell ............ A61K 6/0017 433/228.1 |

FOREIGN PATENT DOCUMENTS

| | | |
|---|---|---|
| DE | 19847635 | 4/2000 |
| EP | 0231420 | 8/1987 |
| EP | 1340472 | 9/2003 |
| EP | 2036533 | 3/2009 |
| EP | 2442778 | 4/2012 |
| JP | 2003-012435 | 1/2003 |
| WO | WO 2002-11678 | 2/2002 |
| WO | WO 2005-016783 | 2/2005 |
| WO | WO 2006-108384 | 10/2006 |
| WO | WO 2007-016295 | 2/2007 |
| WO | WO 2007-047381 | 4/2007 |

(Continued)

OTHER PUBLICATIONS

Houben-Weyl, Methoden der Organischen Chemie, 659 ff (1985).

(Continued)

*Primary Examiner* — Tae H Yoon
(74) *Attorney, Agent, or Firm* — 3M Innovative Properties Compa

(57) ABSTRACT

The invention relates to a curable dental composition comprising a cationically hardenable compound (A) comprising at least two aziridine moieties, a starter (B) being suitable to cure the hardenable compound (A), polymeric particles as filler component (C), the polymeric particles having a maximum particle size of 150 μm or below and the component(s) the polymeric particles are made of being based on fluoropolymers comprising more than 99% monomer repeating units of tetra fluoro ethylene. The invention also relates to the use of such composition for producing a dental impression material or a dental retraction material.

13 Claims, No Drawings

(56) References Cited

FOREIGN PATENT DOCUMENTS

| | | |
|---|---|---|
| WO | WO 2007-104037 | 9/2007 |
| WO | WO 2008-064872 | 6/2008 |
| WO | WO 2009-061884 | 5/2009 |
| WO | WO 2009-151983 | 12/2009 |
| WO | WO 2011-016977 | 2/2011 |
| WO | WO 2011-133495 | 10/2011 |

OTHER PUBLICATIONS

Bartholome, Ullmanns Encyklopadie der technischen Chemie, 469, (1984).
International Search Report for PCT International Application No. PCT/US2015/064365, dated Mar. 4, 2016, 5pgs.

* cited by examiner

CATIONICALLY CURING DENTAL COMPOSITION CONTAINING POLYMERIC PARTICLES AND USE THEREOF

CROSS-REFERENCE TO RELATED APPLICATIONS

This application is the § 371 U.S. National Stage of International Application No. PCT/US2015/064365, filed 8 Dec. 2015, which claims the benefit of European Application No. 14198135.7, filed 16 Dec. 2014, the disclosures of which are incorporated by reference herein in their entireties.

FIELD OF THE INVENTION

The invention relates to a curable composition comprising a cationically hardenable compound with one or more aziridine groups, a starter and polymeric filler particles. The composition is particularly useful for producing dental impression and dental retraction materials.

BACKGROUND

Producing dental replacement parts like crowns and bridges requires the exact determination of the dental situation in the mouth of the patient. Otherwise, the dental replacement parts will not accurately fit.

For determining the dental situation in the mouth of a patient different methods are know. Besides imaging and computer based methods, a huge portion of this task is still accomplished by using conventional dental impression materials.

Dental impression materials can be classified according to their curing mechanism (e.g. addition curing or condensation curing). Dental impression materials can also be classified according to their consistency. Besides low viscous dental impression materials, there exists highly viscous, so-called putty like dental impression materials.

Dental impression materials are typically provided as two component systems which consist of a base and a catalyst paste and which are mixed before use. Different types of chemistry can be employed to formulate dental impression materials.

Often used are polyether impression materials, which cure by a cationic ring-opening polymerization of aziridines (e.g. Impregum™ 3M ESPE), polysiloxanes which cure via a hydrosilation reaction (e.g. Imprint™ 3M ESPE), polysiloxanes which cure via a condensation mechanism (e.g. Xantropren™, Heraeus Kulzer) and mixtures of polyethers and siloxanes which cure via a hydrosilation mechanism (e.g. Senn™, GC).

The curing reaction of the aziridino moieties containing impression material is typically started by mixing a base paste containing the aziridino moieties bearing prepolymer and a catalyst paste containing a strong acid, especially a Lewis acid.

E.g., US 2004/0149164 relates to a mixture of elongated N-alkylaziridine prepolymers which can be used as a dental material. The mixture can contain various modifiers like finely divided fillers, pigments, thixotropic agents and surface-active substances.

U.S. Pat. No. 6,599,960 relates to storage-stable cationically polymerized preparations with improved hardening characteristics. The preparations can contain 0.0005 to 50 wt.-% of soluble and/or fine-particle organic and/or inorganic alkaline earth and/or alkali metal compounds. The preparation can be used for making dental impressions.

U.S. Pat. No. 3,926,636 relates to a light-curable composition consisting of a substance containing at least two aromatic or heteroaromatic o-nitrocarbinol ester groups of a certain structure and a compound having at least two aziridine groups or isocyanate groups. The light-curable composition is particularly suitable for the production of coatings and printing plates.

U.S. Pat. No. 4,167,618 (Schmitt) relates to a polymerization process for aziridine compounds. The polymerization process includes mixing an aziridine compound with an alkyl sulfonium salt.

WO 2011/133495 (3M) describes a radiation curable composition for taking a dental impression comprising a) a cationically hardenable compound comprising at least one aziridine moiety and b) a radiation sensitive starter, the radiation sensitive starter comprising an onium salt, a ferrocenium salt, a combination or mixture thereof.

The materials are typically pasty and cure in the mouth of the patient due to a chemical curing mechanism.

The materials are typically coloured. Colouring the materials is done to address a couple of needs.

From a patient's perspective a nicely coloured material is often more accepted than a non-coloured indifferent mass.

From a practitioner's perspective having a coloured material is desired to have a better contrast in the mouth of the patient, i.e. in order to be able to clearly determine where the material has already been applied and where not. This is even more important, when it has to be ensured that the cured material has been completely removed from the mouth of a patient after curing.

Once removed from the mouth of the patient, the obtained impression represents a negative image of the dental situation.

For producing a dental replacement part, the negative image has to be converted into a positive model or image.

This can be done either by filling the negative mould with plaster to obtain a positive model.

Alternatively, the surface of the negative image is scanned and the electronic data obtained further processed.

However, obtaining a suitable scan showing all the details of the surface of a rubber-elastic material is not easy.

In order to improve scannability of dental impression materials different approaches are meanwhile described.

WO 2008/064872 A2 (Kettenbach) also published as US 2010/0035210 A1 describes a method for producing a dental product, according to which a moulding, in the form of a negative mould, of a tooth or tooth stump is created using a moulding material, and this negative mould is scannned. In this respect, the moulding material may contain titanium oxide, zirconium oxide, zinc oxide and/or barium oxide.

WO 2006/108384 A1 (Dreve) relates to an optimized silicon material for digital optical data acquisition. The silicone material contains a metal oxide powder such as titanium oxide having a particle size below 50 μm.

WO 02/11678 A2 (S&C Polymer) also published as U.S. Pat. No. 7,625,442 describes a kit of parts consisting of a) a material for producing a shaped body and b) a metal powder, a powder of a metal alloy, a powder of a pigment having a metallic effect or a powder having a laminar structure.

DE 198 47 635 A1 (Wacker-Chemie) describes curable dental materials containing organopolysiloxane particles having a mean particle size between 5 and 200 nm. It is stated that the organopolysiloxane particles should be soluble in either of toluene, tetrahydrofuran or water.

All these approaches have in common that a certain amount of inorganic pigment or other light-reflective additive is added.

Adding a highly light-reflective additive, however, affects the brightness of the material. The initially desired colour is weakened and becomes less intense. This is not desired.

Besides the need for a dental material which is nicely coloured and easily scannable, the dental material needs to fulfill other requirements as well.

The above mentioned dental impression compositions based on so-called polyether chemistry curing via N-aziridino moieties are often the preferred choice for the practitioner, if a dental impression with a high accuracy is needed and desired.

However, sometimes removal of the cured composition based on those materials from the mouth of a patient is not easy. Some practitioners and patients rate the cured composition as too hard and/or not elastic enough.

SUMMARY OF INVENTION

It is a general object to provide an improved dental material which addresses one or more of the above issues mentioned in the present text.

In particular, it would be desirable to have a dental material at hand, which can be removed more easily from the mouth of a patient, however, without negatively affecting other desired properties, like consistency.

Alternatively or in addition, the material should be scannable without negatively affecting e.g. the brightness of the colour of the material. It would also be desirable, if the shelf-life of the material is not negatively affected. The invention described in the present text addresses one or more of those needs.

In one embodiment, the invention features a curable dental composition comprising
  a cationically hardenable compound (A) comprising at least one or at least two aziridine moieties,
  a starter (B) suitable to start the curing of compound (A),
  polymeric particles as component (C),
  optionally inorganic filler particles as component (D),
  optionally additives as component (E),
the polymeric particles having a maximum particle size of 150 μm or below and being composed of organic polymers, silicone elastomers or a mixture thereof, filler component (C) being preferably present in an amount from 2 to 70 wt.-% or 2 to 60 wt.-% or 2 to 55 wt.-% with respect to the weight of the whole composition.

In particular, the polymeric particles have a maximum particle size of 150 μm or below and the component(s) the polymeric particles are made of are based on fluoropolymers comprising more than 99% monomer repeating units of tetra fluoro ethylene.

In another embodiment, the invention features a process of producing such a composition comprising a mixing step.

The invention is also directed to a kit of parts comprising Part I and Part II, Part I comprising the cationically hardenable compound comprising at least one or at least two aziridine moieties, the optional inorganic particles and the polymeric particles and Part II comprising the radiation sensitive starter.

A further embodiment of the invention is directed to the use of the composition or kit of parts as described in the present text as or for producing dental impression or dental retraction materials.

Yet a further aspect of the invention is directed to the use of polymeric particles as described in the present text for enhancing the scannability of dental compositions.

Yet another aspect of the invention is directed to the use of polymeric particles as described in the present text for reducing the hardness of a dental composition in its cured state, preferably without affecting its consistency to more than 1 mm or 2 mm in its uncured state.

Unless defined differently, for this description the following terms shall have the given meaning:

The term "compound" or "component" is a chemical substance which has a particular molecular identity or is made of a mixture of such substances, e.g., polymeric substances.

By "paste" is meant a soft, viscous mass of solids dispersed in at least one liquid or a soft, viscous mass of a polymer.

A "particle" or "particulate filler" means a substance being a solid having a shape which can be geometrically determined. The shape can be regular or irregular. Particles can typically be analysed with respect to e.g. grain size and grain size distribution. A particulate filler is composed of free-flowing particles. "Free-flowing" means that the particulate filler can be sieved, that is, it behaves like dry powdered sugar.

"Particle size distribution and maximum particle size" includes the size of agglomerated or aggregated particles. If desired, the maximum particle size can be determined by laser diffraction using a Cilas 1064 Granulometer in "Dry Mode". Results are calculated using the Fraunhofer approximation without Mie correction.

"Polymeric particle" means that the particles have been produced by polymerization (e.g. free-radical polymerization) of monomers comprising polymerizable moieties (e.g. unsaturated moieties). Particles obtained by sol-gel condensation are not considered polymeric particles. Polymeric particles are often granular or spherically shaped.

Polymeric particle(s) include organic polymeric material(s) and/or silicone elastomeric material(s), especially silicone elastomers comprising dimethylsiloxane units.

An "organic polymer" is a macromolecule composed of repeated subunits or moieties. Organic polymers are further characterized by a molecular weight distribution. In contrast to inorganic substances, organic polymers only comprise, contain or consist of the organic elements C, H, N, O, P, S, F, Cl, Br, I as main elements (i.e. more than 50%).

"Elastomeric" means rubber-elastic or rubber-like. Elastomeric materials can be characterized e.g. by a certain tensile strength and/or elongation at break. Other means for characterizing elastomeric materials include the measurement e.g. of the Young's modulus. Elastomeric materials typically have an E-modulus in the range from 0.8 to 10 MPa or from 1 to 8 MPa or from 1.5 to 6 MPa (determined e.g. according to DIN 53504, thickness of sample: 2 mm).

A "silicone elastomer" is an elastomeric polymer comprising silicone units, i.e. comprising the elements Si, O, C and H, in particular dimethylsiloxane ($-O-Si(CH_3)_2-$) units. An "organic polymer" is a macromolecule composed of repeated subunits or moieties. In contrast to inorganic substances, organic polymers only comprise, contain or consist of the organic elements C, H, N, O, P, S, F, Cl, Br, I.

"Non-swellable hardenable composition" means that the composition does not expand during the curing or hardening process by more than 10 or 5 or 1% by volume compared with the initial volume.

"Non-swellable polymeric particles" means that the particles do not show a volume expansion of more than 10 or 5 or 1% by volume within 5 min, if dispersed in water.

A "hardenable compound" is any compound which can be cured or solidified e.g. by chemical crosslinking. Chemical crosslinking can be initiated by using a redox or ionic initiator, radiation or heating thereby typically leading to a significant change in rheological properties like viscosity.

A "starter or initiator" is a substance or a group of substances being able to start or initiate the hardening process of a hardenable compound.

"Radiation sensitive" means that the composition or a part of the composition is sensitive towards radiation and generates or helps to generate reactive species when exposed to the radiation. Those reactive species typically include radicals (charged or not charged), ions and mixtures thereof.

"Radiation curable" means that the composition can be cured or hardened using radiation alone or in combination with other initiators or starters, including redox initiators. The radiation typically comprises wavelength in the range from 250 to 1000 nm or from 350 nm to 700 nm.

The terms "vulcanizing", "hardening", "polymerizing", "crosslinking", "curing" and "setting" are used interchangeable and refer to compositions that have as a common attribute the development of a crosslinked polymer from relatively low molecular weight linear or branched polymers or pre-polymers by means of a chemical reaction that simultaneously forms these crosslinks and effectively extends chain length at room temperature.

"(Meth)acryl" means "acryl" and "methacryl".

"Urethane" means a moiety with the structural element "—O—CO—NH—".

"Poly" means that the respective substance contains at least 10 repeating units of a certain monomer moiety.

The term "crosslinked polymer" refers to polymers that are the result of the reaction of the functional group or groups of the polymer chains or prepolymers that were lengthened or connected, e.g., to form a crosslinked network. In contrast to a thermoplastic polymer (i.e., a polymer that softens and flows upon heating) a crosslinked polymer, after crosslinking, is characteristically incapable of further flow.

The term "cationically polymerizable compound" is defined as a compound which can be polymerised using an initiator containing or being able to generate cations, especially reactive cations.

A "prepolymer" is defined as a compound or a mixture of compounds obtainable by polymerization (such as e.g. polycondensation reaction) of monomers resulting in an intermediate product or mixture of products with increased molecular weight compared to the monomers used. The resulting intermediate product itself bears functional groups (either left over from the initial polymerization or introduced afterwards). The prepolymer containing functional groups can be used for further polymerization reactions (such as e.g. polycondensation reaction or polyaddition reaction) leading to a polymer or polymer mixture or a crosslinked polymer with increased molecular weight compared to the prepolymer.

"Aziridines" are a group of organic compounds sharing the aziridine functional group, which is a three membered heterocycle with one amine group and two methylene groups. The parent compound of the aziridines is called aziridine with molecular formula $C_2H_5N$.

An "alkyl-substituted aziridino group" is an aziridine group, wherein at least one of the hydrogen atoms of the methylene groups is substituted by an alkyl group, preferably by a C1 to C4 alkyl group, e.g. methyl, ethyl, n- and iso-propyl or n-, iso- or tert.-butyl group. In the chemical literature a "methyl substituted aziridine" is sometimes also referred to as "propylene imine".

"Polyether" or "polyether group containing compound" are compounds having a molecular weight of at least 150 g/mol and containing in the backbone at least 3, 10 or 20 ether moieties. Polyether containing compositions used as dental impression material can be cured by different mechanisms. Widely used is a crosslinking reaction using aziridine groups.

Examples of polyether groups containing impression materials are given in U.S. Pat. No. 5,569,691, US 2004/0146713 A1 and US 2006/0069180. Commercially available materials are sold e.g. under the brand Impregum™ (3M ESPE).

By "derivative" is meant a chemical compound showing a chemical structure closely related to the corresponding reference compound and containing all featured structural elements of the corresponding reference compound but having small modifications like bearing in addition comparably small additional chemical groups like e.g. $CH_3$, Br, Cl, or F or not bearing comparably small chemical groups like e.g. $CH_3$ in comparison to the corresponding reference compound. A derivative of a certain compound comprises the chemical structure of that compound, but may contain other side groups or moieties.

The following examples might illustrate this: tetramethyl bis-phenol A bearing four additional methyl groups with respect to the reference compound bis-phenol A, and bis-phenol F not bearing two additional methyl groups with respect to the reference compound bis-phenol A are derivatives of bis-phenol A within the meaning of this definition.

"Room temperature curable" implies that the curing reaction can proceed at temperatures at or near 25° C. For example, the oral cavity of the mouth has an average temperature of approximately 32° C. and is therefore near room temperature. Certain "high" temperature cured materials are designed to cure only at relatively high temperatures (e.g., >50° C. or >100° C.) and are stable (i.e., the curing reaction is retarded) at room temperature for prolonged periods. The compositions of the invention are room temperature vulcanizing.

A "dental composition" or a "composition for dental use" or a "composition to be used in the dental field" is any composition which can be used in the dental field. In this respect the composition should not be detrimental to the patients' health and thus free of hazardous and toxic components being able to migrate out of the composition.

Examples of dental compositions include permanent and temporary crown and bridge materials, artificial crowns, anterior or posterior filling materials, adhesives, mill blanks, lab materials and orthodontic devices.

Dental compositions are typically hardenable compositions, which can be hardened at ambient conditions, including a temperature range from about 15 to 50° C. or from about 20 to 40° C. within a time frame of about 30 min or 20 min or 10 min. Higher temperatures are not recommended as they might cause pain to the patient and may be detrimental to the patient's health.

Dental compositions are typically provided to the practitioner in comparable small volumes, that is volumes in the range from about 0.1 to about 500 ml or from about 0.5 to about 100 ml or from about 1 to about 50 ml. Thus, the storage volume of useful packaging devices is within these ranges.

A "dental impression" may be described as an accurate representation of part or all of a person's dentition. It forms a "negative" of a person's hard dental tissue which can then be used to make a model (physical) of the dentition. This may be used for the fabrication of dentures, crowns or other prostheses. An impression is typically carried out by placing a viscous material into the mouth in a customised or stock tray. The material then sets to become an elastic solid, and when removed from the mouth retains the shape of the teeth and gingiva.

A "dental impression material" is a material used for making impressions of the tooth structure. A dental impression material is usually applied on a dental impression tray. A dental impression material can be based on different chemical substances and crosslink by various chemical reactions. Common materials used for dental impressions include alginate, agar, polyethers including aziridine substituted polyether materials as well as silicones, both condensation-cured silicones and addition-cured silicones including polyvinyl siloxanes (so-called VPS materials).

The term "dental impression materials" comprises precision impression materials, situation impression materials, bite registration materials, duplicating materials (applicable for the duplication of master models, e.g. for all-ceramic restorations requiring a refractory investment model and when inlays, onlays, cantilevers and other precision attachments are being fabricated) and modelling materials (applicable for e.g. reconstructing the gingival, producing crowns and bridges). Duplicating and modelling materials are commercially available e.g. from 3M ESPE under the trademarks or Vestogum™.

A "putty like dental impression material" is a kneadable dental impression material having a consistency of 35 mm or below according to ISO 4823.

The term "automixer-suitable impression material" relates to a multi-component impression material which can be dispensed, for example, from a two-component disposable cartridge through a static mixer, e.g., of SulzerMixpac Company (U.S. Pat. No. 5,464,131, US 2001/0004082) or from tubular film bags in dual-chamber reusable cartridges through a dynamic mixer, e.g., in the "Pentamix™", "Pentamix™ 2" and "Pentamix™ 3" devices of 3M ESPE Company (cf. U.S. Pat. Nos. 5,286,105 and 5,249,862).

A "dental retraction material" is a material intended to be placed in the gingival sulcus, that is, the natural space between the hard dental tissue (i.e. tooth structure) and the gum tissue that surrounds the hard dental tissue. Once placed in the gingival sulcus, the dental retraction material will exert pressure on the surrounding tissue resulting in a widening of the gingival sulcus to enable the practitioner to get a more precise impression of the dental situation below the gum line during a dental impression process. Like a dental impression material, a dental retraction material is removed from the mouth of the patient after use.

The term "dental tissue" includes the hard tooth substance (enamel and dentin), the gingival region (soft dental tissue) surrounding the hard tooth substance and hard tooth substance bearing orthodontic appliances.

A "temporary crown and bridge material" within the meaning of the invention is a hardenable material used for making dental crowns and bridges. These materials are typically used during the time period a dental technician needs for producing a permanent prosthetic work such as a crown or bridge. These time periods can last from a few days (1 to 6 days), a few weeks (1 to 4 weeks) or a few months (1 to 6 month).

A "surfactant" is an agent imparting wettability to a material, that is making the material more wettable compared to a material not containing a surfactant. The wettabilty can be determined by the water contact angle which can be measured using e.g. a goniometer DSA 10 (Kruss). A low water contact angle indicates a better wettability.

"Molecular weight" in the context of the invention and if not otherwise indicated always means number average molecular weight ($M_n$). The molecular weight (Mn) of the polymerizable compound before setting can be determined using nuclear magnetic resonance spectroscopy (end-group determination). In this respect proton ($^1H$) NMR techniques are employed to estimate the molecular weight of the precursor of the prepolymer. Integrated signals of the terminal —$CH_2$— groups are compared to the integrated sum of proton signals from backbone hydrocarbon protons taking into account co-monomer ratio, if applicable. To achieve appropriate separation of terminal methylene proton signals from the backbone proton signals, terminal hydroxyl groups are esterified with trifluoroacetic acid.

"Ambient conditions" within the meaning of the invention mean the conditions which the inventive solution is usually subjected to during storage and handling. Ambient conditions may for example: be a pressure of 900 to 1100 mbar, a temperature of –10 to 60° C. and a relative humidity of 10 to 100%. In the laboratory ambient conditions are adjusted to 23° C. and 1013 mbar.

A composition or solution is "essentially or substantially free of" a certain component within the meaning of the invention, if the composition or solution does not contain said component as an essential feature. Thus, said component is not wilfully added to the composition or solution either as such or in combination with other components or ingredient of other components. A composition being essentially free of a certain component usually contains the component in an amount of less than 1 wt.-% or less than 0.1 wt.-% or less than 0.01 wt.-% with respect to the whole composition. Ideally the composition does not contain the said component at all. However, sometimes the presence of a small amount of the said component is not avoidable e.g. due to impurities.

As used herein, "a", "an", "the", "at least one" and "one or more" are used interchangeably. The terms "comprises" or "contains" and variations thereof do not have a limiting meaning where these terms appear in the description and claims.

Also herein, the recitations of numerical ranges by endpoints include all numbers subsumed within that range (e.g., 1 to 5 includes 1, 1.5, 2, 2.75, 3, 3.80, 4.5, etc.).

"Comprise" includes the terms "contain", "essentially consists of" and "consists of".

Unless otherwise indicated, all numbers expressing quantities of ingredients, measurement of properties used in the specification and claims are to be understood as being modified in all instances by the term "about". Any numerical value, however, inherently may contain certain errors necessarily resulting from the standard deviations found in their respective testing measurements.

DESCRIPTION OF INVENTION

It has been found that the dental composition described in the present text fulfils the practitioners' needs especially with regard to properties like scannability, colour brightness, removability, elongation at break, curing time or combinations thereof.

It was found that the surface of the dental composition comprising polymeric particles is sufficient reflective without negatively affecting its colour brightness.

On the one hand this allows an easy detection of the composition in the mouth of a patient during application of the curable composition and removal of the cured composition.

On the other hand the surface of the cured composition can be scanned with sufficient accuracy.

Further, depending on the amount of polymeric particles present, the dental composition in its cured state has not only a reduced hardness but also shows an improved elongation at break.

This is beneficial not only for the patient but also for the dentist as it allows an easier removal from the mouth of a patient, even if there are undercuts in the dentition.

It was also found that overall the consistency of the composition is not negatively affected.

In particular, it was found that by replacing inorganic filler particles of a given formulation by polymeric particles, the hardness of a cured dental composition can be reduced, although the consistencies of the pastes to be mixed for obtaining the curable dental composition remain essentially unaffected before mixing.

Thus, the present invention enables the formulation of a composition having a high filler load and thus a high consistency without negatively affecting the Shore hardness.

The composition can not only be mixed in a conventional way, either by hand or using a mixing device, either manually driven or automated, but also applied by using the impression techniques familiar to the dental practitioner.

In addition, the composition described in the present text can be cured at ambient conditions, including room temperature.

According to one embodiment, the composition described in the present text can be cured on demand. That is, the practitioner has the time he needs for applying the curable composition on a substrate or surface. If he is satisfied, he can start the curing process by applying radiation.

Thus, a curable composition can be provided where the curable components are present together with the starter(s) in mixture. Absent radiation, the mixture remains storage stable. However, upon radiation the mixture starts to cure.

Certain embodiments of the curable composition can be characterized by at least one or more of the following features before hardening:

Consistency (according to ISO 4823): 0, 1, 2 or 3;
Setting time: showing a Shore hardness A of at least 20 within 15 min after mixing of the components of the composition at ambient conditions (e.g. 23° C.).

The consistency which can be achieved is typically with the range commercial impression materials have. These consistencies are usually classified as follows (ISO 4823):
consistency 3: corresponding to at least 36 mm;
consistency 2: corresponding to 31 to 41 mm;
consistency 1: corresponding to utmost 35 mm;
consistency 0: corresponding to utmost 35 mm.

Certain embodiments of the hardened composition can be characterized by at least one or more of the following features:
Tensile strength (according to DIN 53504): at least 1.2 MPa, or at least 1.5 or from 1.2 to 10 or from 1 to 7 MPa;
Elongation at break (according to DIN 53504): at least 100%, or at least 150%, or at least 250%;
Recovery from deformation (according to ISO 4823): at least 90%, or at least 95%, or at least 98%;
Shore A hardness (according to DIN 53505; 24 h): below 70 or below 65 or below 60 or within a range from 20 to 70 or from 25 to 65 or 30 to 60;
Curing time: Shore hardness A of at least 20, of at least 25, or at least 30 within 15 min at 23° C.

If desired, the respective properties can be determined as outlined in the Example section.

The cationically hardenable compound according to component (A) typically comprises a backbone and at least one reactive functional group.

The backbone of the cationically hardenable compound typically comprises moieties selected from polyether, polyester, polyurethane, silicone, polyalkylene, polystyrol, polysulfide and combinations thereof.

In the dental field a polyether moieties containing backbone can be preferred. Those groups typically also improve the hydrophilic properties of the composition.

According to one embodiment, the cationically hardenable compound includes a polyether group containing hardenable prepolymer as component (A) or part of component (A), that is, a prepolymer comprising a polyether group(s) and reactive moieties which upon addition of a suitable catalyst or initiator can react with each other and thus form a polymeric network.

The molecular weight (Mn) of the polyether group(s) containing prepolymer is typically in a range from 150 to 20,000 g/mol, or in the range from 250 to 10,000 g/mol, determined e.g. with GPC methods know to the person skilled in the art.

Suitable polyethers or polyether groups, which can be used, include those which meet the requirements in terms of material properties with regard to the preferred use as dental materials.

Appropriate polyethers or polyether groups can be produced in a manner known to the person skilled in the art by the reaction of the starting compound having a reactive hydrogen atom with alkylene oxides, for example ethylene oxide, propylene oxide, butylene oxide, styrene oxide, tetrahydrofurane or epichlorohydrine or mixtures of two or more thereof.

Especially suitable are polyether compounds which are obtainable by polyaddition of ethylene oxide, 1,2-propylene oxide, 1,2-butylene oxide or tetrahydrofuran or of mixtures of two or more of the mentioned compounds with the aid of a suitable starting compound and a suitable catalyst.

The reaction products of low-molecular-weight polyfunctional alcohols having at least two hydroxyl groups with alkylene oxides, so-called polyethers, may also be used as polyols. The alkylene oxides preferably have from 2 to 4 carbon atoms. Suitable polyols are, for example, the reaction products of ethylene glycol, propylene glycol, butanediol or hexanediol isomers with one or more of the following alkylene oxides: ethylene oxide, propylene oxide or butylene oxides like tetrahydrofurane. Furthermore, the reaction products of polyfunctional alcohols such as glycerol, trimethylolethane or trimethylolpropane, pentaerythritol or sugar alcohols, or mixtures of two or more thereof, with the mentioned alkylene oxides, forming polyether polyols are also suitable.

Suitable starting compounds are, for example, water, ethylene glycol, 1,2- or 1,3-propylene glycol, 1,4- or 1,3-butylene glycol, 1,6-hexanediol, 1,8-octanediol, neopentyl glycol, 1,4-hydroxymethylcyclohexane, 2-methyl-1,3-propanediol, glycerol, trimethylolpropane, 1,2,6-hexanetriol, 1,2,4-butanetriol, trimethylolethane, pentaerythritol, mannitol, sorbitol, or mixtures of two or more thereof.

Especially suitable are polyether compounds as are obtainable by polyaddition of ethylene oxide, 1,2-propylene oxide, 1,2-butylene oxide or tetrahydrofuran or of mixtures of two or more of the mentioned compounds with the aid of a suitable starting compound and a suitable catalyst.

For example, polyether polyols which are prepared by copolymerisation of tetrahydrofuran and ethylene oxide in a molar ratio of from 10:1 to 1:1, preferably to 4:1, in the presence of strong acids, for example boron fluoride etherates, are suitable.

The dental composition comprises at least a cationically hardenable compound having at least 1 aziridine moiety or more, if desired, e.g. at least 2 or 3 or 4 or 5 or 6 aziridine moieties. Using a cationically hardenable compound with at least 2 azirdine moieties can be preferred to ensure a sufficient crosslinking.

According to another embodiment, the cationically hardenable compound comprises on average at least 2 aziridine moieties.

The term "on average" is to be interpreted such in the context of the present text that a mixture of a large number of compounds may comprise both compounds having less than 2 aziridino groups and also compounds having more than 2 aziridine groups although, when seen over the entirety of the compounds of component (A), the average functionality of all molecules is, with respect to aziridine groups, 2 or more.

All mentioned types of polyaddition or polycondensation products can be provided with aziridine groups by means of any desired subsequent reactions known to the person skilled in the art. For example, it is possible first to introduce, into an appropriate polymer, sub stituents which are in turn capable of reacting with suitable aziridine derivatives.

It is also possible to polymerise cyclic ethers, preferably epoxides, onto the chain so that products are obtained which at the end contain substituents which can react with aziridine. There come into consideration, for example, polyethers onto which halo-substituted epoxides, e.g. epibromohydrin, are polymerised.

Suitable possible methods for providing the polymers with aziridine groups are mentioned, e.g., in U.S. Pat. No. 3,453,242.

Suitable polymers carry the aziridine groups terminally or laterally, or terminally and laterally, but preferably terminally.

The aziridine groups containing compound typically have a dynamic viscosity 11 of from 10 to 500 Pa*s, especially from 15 to 300 Pa*s. A preferred viscosity range is from 20 to 180 Pa*s at 23° C.

The aziridine equivalent is typically from 250 to 25,000 g/equivalent, especially from 400 to 10,000 g/equivalent. The term "aziridine equivalent" is defined as (molecular mass of the molecule)/(number of aziridine groups present in the molecule).

Using compounds having such an aziridine equivalent weight may facilitate the provision of rubber-like or elastomeric materials (after hardening). Compounds having an aziridine equivalent weight outside this range might either be too hard or brittle or too soft, e.g. do not have the desired Shore hardness or tensile strength.

The cationically hardenable compound which can be used may comprise only one type of aziridine group containing polymer. It is, however likewise possible for the cationically hardenable compound to comprise two or more different types of aziridine polymers, for example 3, 4 or 5 different types.

A "type of polymer" is understood, in the context of the present invention, to be a polymer as results from the polyaddition or polycondensation of selected monomers under the selected reaction conditions. A type of polymer can accordingly include polymer molecules of differing chemical constitution and differing molecular weight, depending on the reaction conditions selected. However, two reactions carried out using identical monomer compositions under identical reaction conditions always result, in accordance with the invention, in identical types of polymer. Two reactions which are carried out using identical monomers but under different reaction conditions may result in identical types of polymers but need not do so. The crucial factor therein is whether there are identifiable differences—in terms of chemical constitution, molecular weight and further parameters which can be determined—that are of relevance to the material properties. Two reactions which are carried out using different monomer compositions always result, in accordance with the invention, in different types of polymers.

Reactive side groups which pending from or attached to the backbone of the prepolymer include those characterized by the following formula (I)

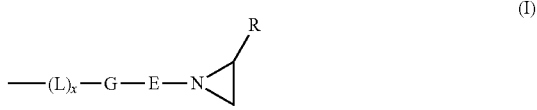

wherein
R represents H, C1-C12 alkyl, C2-C12 alkenyl, C2-C12 alkinyl, C7-C15 alkylaryl, C7-C15 arylalkyl, C3-C12 cycloalkyl, and wherein hydrogen atoms may be replaced by Cl or F and/or wherein up to five carbon atoms may be replaced by atoms or group of atoms selected from O, CO, N, S,
E represents a C1-C18 branched or unbranched hydrocarbon chain wherein up to five carbon atoms may be replaced by atoms or group of atoms selected from O, CO, N, S,
G represents a group selected from C(O)O, C(O)NR, C(O), C(O)C(O), C(O)(CH2)mC(O) with m=1 to 10, C(S)NR, CH2,
L represents O, S, NR with x=0 or 1.

It can be preferred, if the cationically hardenable compound has a linear molecular structure. Thus, the cationically hardenable compound may typically comprise a linear backbone, which is typically end-capped with aziridine groups. Usually, there are no side chains, especially cationically hardenable side chains pending from the backbone.

The cationically hardenable compound is typically present in an amount, which allows the formation of a sufficiently crosslinked network, in order to fulfil the practitioners needs.

The cationically hardenable compound is typically present in an amount of at least 5 wt.-% or at least 12 wt.-% or at least 20 wt.-%, wt.-% with respect to the whole composition.

The cationically hardenable compound is typically present up to an amount of 95 wt.-% or up to 80 wt.-% or up to 75 wt.-%, wt.-% with respect to the whole composition.

Typical ranges include from 5 wt.-% to 90 wt.-% or from 12 wt.-% to 80 wt.-% from 25 wt.-% to 70 wt.-%, wt.-% with respect to the whole composition.

By varying the amount of the cationically hardenable compound, e.g. the viscosity and the hardness of the cured composition can be adjusted.

If the amount of the cationically hardenable compound is too low, the resulting composition might not cure within the desirable period of time or might show not desirable mechanical properties.

If the amount of the cationically hardenable compound is too high, the resulting composition might be too viscous.

If desired, besides the cationically curable compound containing at least two aziridine groups, further curable compounds can be present being different from the cationically hardenable compound described above.

Thus, blends of various cationically polymerizable resins are also contemplated in this invention. Examples of such blends include two or more weight average molecular weight distributions of resin-containing compounds, such as low molecular weight (below 200), intermediate molecular weight (200 to 10,000) and higher molecular weight (above 10,000).

Alternatively or additionally, the resin may contain a blend of resin-containing materials having different chemical natures, such as aliphatic and aromatic, or functionalities, such as polar and non-polar. Other cationically polymerizable polymers may additionally be incorporated, if desired.

The curable composition contains a starter as component (B) being able to start the hardening reaction of the cationically hardenable compound comprising at least one or two aziridine moieties.

Useful starters typically include Lewis acids or Broensted acids. In principle both organic and inorganic acids can be used.

Particular useful initiators include sulfonium salts, especially alkyl sulfonium salts or sulfonium salts derived from glutaconic acid. Those and others are described e.g. in WO 2007/016295 (Klettke et al.) or U.S. Pat. No. 4,167,618 (Schmitt et al.). The content of these documents as regards initiators is explicitly mentioned and herewith incorporated by reference.

Suitable sulfonium acids and salts thereof include 4-toluenesulphonic acid, 4-phenol sulphonic acid, 4-bromobenzenesulphonic acid, 4-chlorobenzenesulphonic acid, benzenesulphonic acid, alkylbenzenesulphonic acids, in particular dodecylbenzenesulphonic acid, naphthalene-2-sulphonic acid and alkanesulphonic acids.

Other starters which can be used include strong acids such as hexafluoroantimonic acid, hexafluorophosphoric acid or tetrafluoroboric acid.

The use of phosphonic acids such as vinylphosphonic acid and propylphosphonic acid is also possible. Polymeric acids such as polyvinylphosphonic acid, polyacrylic acid, copolymeric acids, prepared from maleic anhydride with other monomers can also be used, if desired.

Furthermore, saturated and unsaturated carboxylic acids such as propionic acid, succinic acid, tartaric acid, trimellitic acid, benzoic acid, phenylacetic acid, citric acid, maleic acid, adipinic acid, o-chlorobenzoic acid or reaction products of polyvalent alcohols and acid anhydrides such as maleic anhydride and succinic anhydride can also be used.

Those and other starters are described e.g. in US 2003/153726 (Eckhardt et al.). The content of this document as regards initiators is explicitly mentioned and herewith incorporated by reference.

If desired, the acids described above can be used in combination with one or more antacid-acting components.

Suitable antacid-acting components which can be used include oxides, hydroxides, carbonates and carboxylates of the elements aluminum, chromium, copper, germanium, manganese, lead, antimony, tin, tellurium, titanium and zinc, with aluminum and zinc being sometimes preferred.

In particular, the addition of zinc components such as zinc hydroxide, zinc oxide, zinc carbonate or mixtures of these components can be advantageous, e.g. for improving the storage stability of the composition, e.g. by reducing corrosion of the packaging material during storage of the composition.

With respect to certain compositions it was also found that adding in particular antacid-acting components containing Zn, the mechanical properties of the hardened composition can be improved.

If an antacid-acting component is added, the ratio between starter component (B) and the antacid-acting component is typically within a range from 0.5 to 2.0 or from 0.7 to 1.2 antacid-acting equivalents to one acid equivalent for starter component (B).

This initiator can be used in an amount of at least 1 wt.-% or at least 2 wt.-% or at least 3 wt.-% with respect to the weight of the whole composition.

The initiator can be used up to an amount of at least 30 wt.-% or at least 20 wt.-% or at least 10 wt.-% with respect to the weight of the whole composition.

Thus, the initiator can be used in an amount from 1 to 30 wt.-% or from 2 to 20 wt.-% or from 3 to 10 wt.-% with respect to the weight of the whole composition.

According to another embodiment, the starter according to component (B) is a radiation sensitive starter.

This starter is typically able to produce cations (e.g. including $H^+$) when exposed to radiation. Such a radiation sensitive starter, it is sometimes characterized as a latent Lewis acid source.

According to one embodiment, the radiation sensitive starter can be characterized by at least one or more of the following features:

Molecular weight: being in a range from 350 to 2000 or from 400 to 1400,

Reduction potential E1/2red (On+) of the onium salt: at least −1.1 Volt vs. SCE (Standard calomel electrode), or at least −0.5 Volt vs. SCE or at least −0.3 Volt vs. SCE.

Radiation sensitive starters which were found to be useful include onium salts, ferrocenium salts and mixtures thereof as long as they are radiation sensitive.

In this respect it should be noted that not all onium salts are radiation sensitive. E.g. the sulfonium salts described in U.S. Pat. No. 4,167,618, US 2005/200585, US 2006/106127 are not radiation sensitive. Those salts do not generate reactive species upon exposure to radiation with a wavelength in the range from 250 to 1,000 nm or within the spectrum visible to the human eye.

A particularly useful class of radiation sensitive starters include onium salts, especially iodonium salts or sulfonium containing low or non-coordinating anions. Low or non-coordinating anions include $BF_4^-$, $PF_6^-$, $SbF_6^-$, $AsF_6^-$, $SbF_5OH^-$, $B(C_6F_5)_4^-$, $B(C_6(CF_3)_5)_4^-$, $B(C_6H_2(CF_3)_3)_4^-$.

Sulfonium salts which can be used include those bearing two or three aryl groups (including C1 to C8 substituted aryl and phenyl) attached to the sulfonium ion. Sulfonium salts, where the sulfonium ion bears an alkyl group are not useful, as those are typically not radiation sensitive.

Particularly, diaryliodonium salt(s) were found to be useful.

It can be advantageous, if the iodonium salt is soluble in the composition and preferably is shelf-stable, meaning it does not spontaneously promote polymerization when dissolved therein in the presence of the visible light sensitizer and the electron donor compound or without these additional components.

Accordingly, selection of a particular iodonium salt may depend to some extent upon the particular resin, and the optionally present visible light sensitizer and/or electron donor. Suitable iodonium salts are described in U.S. Pat. Nos. 3,729,313, 3,741,769, 3,808,006, 4,250,053 and 4,394,403. The iodonium salt can be a simple salt, containing an anion such as $Cl^-$, $Br^-$, $I^-$ or $C_2H_5SO_3^-$; or a metal complex salt containing an antimonate, arsenate, phosphate or borate such as $SbF_5OH^-$ or $AsF_6^-$. Combinations of iodonium salts can be used if desired.

The diaryliodonium compounds may have the following structure (II):

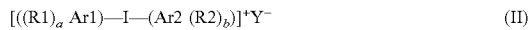

$$[((R1)_a\ Ar1)-I-(Ar2\ (R2)_b)]^+Y^- \quad (II)$$

with Ar1 and Ar2 being independently of each other substituted or unsubstituted, fused or non-fused aromatic systems having 4 to 20 C atoms, including, for example, phenyl, tolyl, cumyl, anisyl, chlorophenyl, nitrophenyl, naphthyl, thienyl, furanyl and pyrazolyl, wherein R1 and R2 are identical or different and independently of each other denote an H atom, an aliphatic radical having 1 to 19, preferably 1 to 9 C atoms, it being possible for one or more C atoms to be replaced by O, C=O, O(C=O), F, Cl, Br, $SiR3_3$ and/or $NR3_2$ wherein R3 is an aliphatic radical having 1 to 7 C atoms, in which one or more C atoms can be replaced by O, C=O and/or O(C=O), and a and b independently of each other can be 1 to 5. The aromatics Ar1 and Ar2 can be bonded to one another via R1 and/or R2.

The counter-anion $Y^-$ is typically an anion of low nucleophilicity having the following structure (III):

$$K_x\ L_y \quad (III)$$

wherein K is an element of main group III, V or VII, such as, for example, B, Al, P, Sb, As or I, and x can assume numerical values from 1 to 4, L independently of one another denotes aromatic, aliphatic, araliphatic or cycloaliphatic radicals having 1-25 C atoms, in which one or more C atoms can be replaced by F, Cl, Br or I, and y can assume numerical values from 0 to 6. Preferred radicals L are pentafluorophenyl, tetrafluorophenyl, trifluorophenyl, fluorophenyl, phenyl, 4-trifluoromethyl phenyl, 3,5-bis (trifluoromethyl)phenyl, 2,4,6-tris(trifluoromethyl)-phenyl, fluorine and iodine. Particularly preferred counter-ions $Y^-$ are $PF6^-$, $SbF6^-$ and $B(C_6\ F_5)_4^-$.

Examples of useful aromatic iodonium complex salt photoinitiators include: diphenyliodonium tetrafluoroborate; di(4-methylphenyl)iodonium tetrafluoroborate; phenyl-4-methylphenyliodonium tetrafluoroborate; di(4-heptylphenyl)iodonium tetrafluoroborate; di(3-nitrophenyl)iodonium hexafluorophosphate; di(4-chlorophenyl)iodonium hexafluorophosphate; di(naphthyl)iodonium tetrafluoroborate; di(4-trifluoromethylphenyl)iodonium tetrafluoroborate; diphenyliodonium hexafluorophosphate; di(4-methylphenyl)iodonium hexafluorophosphate; diphenyliodonium hexafluoroarsenate; di(4-phenoxyphenyl)iodonium tetrafluoroborate; phenyl-2-thienyliodonium hexafluorophosphate; 3,5-dimethylpyrazolyl-4-phenyliodonium hexafluorophosphate; diphenyliodonium hexafluoroantimonate; 2,2'-diphenyliodonium tetrafluoroborate; di(2,4-dichlorophenyl) iodonium hexafluorophosphate; di(4-bromophenyl)iodonium hexafluorophosphate; di(4-methoxyphenyl)iodonium hexafluorophosphate; di(3-carboxyphenyl)iodonium hexafluorophosphate; di(3-methoxy-carbonylphenyl)iodonium hexafluorophosphate; di(3-methoxysulfonylphenyl)iodonium hexafluorophosphate; di(4-acetamidophenyl)iodonium hexafluorophosphate; di(2-benzothienyl)iodonium hexafluorophosphate; and diphenyliodonium hexafluoro-antimonate.

Of the aromatic iodonium complex salts which are suitable for use in the compositions of the invention diaryliodonium hexafluorophosphate, diaryliodonium hexafluoroantimonate, 4-octyloxyphenyl phenyliodonium hexafluoroantimonate, 4-(2-hydroxytetradecyloxyphenyl) phenyliodonium hexafluoroantimonate, and 4-(1-methylethyl) phenyl 4-methylphenyliodonium tetrakis(pentafluorophenyl)borate are among the preferred salts. These salts are preferred because, in general, they promote faster reaction, and are more soluble in inert organic solvents than are other aromatic iodonium salts of complex ions.

The aromatic iodonium complex salts may be prepared by metathesis of corresponding aromatic iodonium simple salts (such as, for example, diphenyliodonium bisulfate). Thus, for example, the complex salt diphenyliodonium tetrafluoroborate can be prepared by the addition at 60° C. of an aqueous solution containing 29.2 g silver fluoroborate, 2 g fluoroboric acid, and 0.5 g phosphorous acid in 30 ml of water to a solution of 44 g (139 millimoles) of diphenyliodonium chloride. The silver halide that precipitates is filtered off and the filtrate concentrated to yield diphenyliodonium fluoroborate which may be purified by recrystallization.

The aromatic iodonium simple salts may be prepared by various methods including (1) coupling of two aromatic compounds with iodyl sulfate in sulfuric acid, (2) coupling of two aromatic compounds with an iodate in acetic acid-acetic anhydride-sulfuric acid, (3) coupling of two aromatic compounds with an iodine acetate in the presence of an acid, and (4) condensation of an iodoso compound, an iodoso diacetate, or an iodoxy compound with another aromatic compound in the presence of an acid. Diphenyliodonium bisulfate is prepared by method (3), for example, by the addition over a period of eight hours at below 5° C. of a mixture of 35 ml of conc. sulfuric acid and 50 ml of acetic anhydride to a well-stirred mixture of 55.5 ml of benzene, 50 ml of acetic anhydride, and 53.5 g of potassium iodate. The mixture is stirred for an additional four hours at 0°–5° C. and at room temperature (25° C.) for 48 hours and treated with 300 ml of diethyl ether. On concentration, crude diphenyliodonium bisulfate precipitates and may be purified by recrystallization if desired.

Besides onium salts also ferrocenium salts were found to be useful.

Ferrocenium salts which can be used include those represented by the following formula (IV):

$$[R^1_a(C_6H_n)Fe(C_5H_m)R^2_b]^+Y^- \quad (IV)$$

with n=1,2,3,4,5; m=1,2,3,4; a=1,2,3,4,5; b=1,2,3,4;
n+a=6; m+b=5;
$R^1$=H, C1 to C6 alkyl; $R^2$=H, C1 to C6 alkyl; Y=as defined above.

Specific examples for ferrocenium salts which can be used include eta-6-Cumol eta-5-cyclopentadienyl iron-hexafluorophosphate, eta-6-Cumol eta-5-cyclopentadienyl iron-hexafluoroantimonat, eta-6-Cumol eta-5-cyclopentadienyl iron-tetrafluorborat. Cumol or cumene has the formula $C_6H_5CH(CH_3)_2$.

The molar ratio between the starter and the cationically hardenable compound includes ranges from 1.0:0.1 to 1.0:20.0, or from 1.0:0.5 to 1.0:10.0, or from 1.0:0.8 to 1.0:30.

As the starter does not only act as a catalyst but chemically react—to a certain extend—with the hardenable composition, a sufficient amount of initiator should be present.

The amount of the starter to be used is not particularly limited, unless the desired curing reaction cannot be achieved.

The starter is typically present in an amount of at least 0.1 wt.-% or at least 0.5 wt.-%.

The starter is typically present up to an amount of 50 or up to 35 wt.-% or up to 20 wt.-%.

Typical ranges for this kind of starter include from 0.25 wt.-% to 50 wt.-% or from 0.5 wt.-% to 40 wt.-% from 1 wt.-% to 25 wt.-%, wt.-% with respect to the weight of the whole composition.

If the amount of the starter is too low, the desired depth of cure may not be obtained.

Adding a further initiator or starter or a combination of starts can sometimes be beneficial for improving or enhancing the depth of cure.

It can be beneficial, if the cationically curable composition can be cured by using visible light, that is, with radiation having a wavelength in the range from 380 to 800 nm or from 400 to 500 nm.

In this case, it is recommended that a sensitizer, especially a visible light sensitizer is present.

A "sensitizer" is defined as a compound or a combination of compounds which are able to absorb the radiation in the emitted wavelength or in a region of the emitted wavelength and to generate the initiating species of the polymerization reaction.

According to one embodiment, the sensitizer may have a molecular weight: being in a range from 50 to 1000 or from 100 to 800.

The sensitizer should be partly, essentially or completely soluble in the photopolymerizable composition, free of functionalities that would substantially interfere with the cationic polymerization process, and capable of light absorption somewhere within the range of wavelengths between 400 and 1000 nanometers (nm). Preferred visible light sensitizers contain one or more carbonyl functional groups.

Suitable visible light sensitizers may include compounds in the following categories: ketones, coumarin dyes (e.g., ketocoumarins), xanthene dyes, fluorone dyes, fluorescein dyes, aminoketone dyes, and p-substituted aminostyryl ketone compounds. Ketones (e.g., monoketones or alpha-diketones), coumarin dyes (e.g., ketocoumarins), xanthene dyes, fluorone dyes, and fluorescein dyes are particularly preferred visible light sensitizers for use in the invention. For applications requiring deep cure, it is preferred to employ sensitizers having an extinction coefficient below 1000 lmole$^{-1}$cm$^{-1}$, more preferably or below 100 lmole$^{-1}$cm$^{-1}$, at the desired wavelength of irradiation for photopolymerization.

The alpha-diketones are an example of a class of visible light sensitizers having this property, and are particularly preferred for dental applications.

By way of example, a preferred class of ketone visible light sensitizers has the formula (V):

ACO(X)$_b$B (V)

where X is CO or CR$^1$R$^2$ where R$^1$ and R$^2$ can be the same or different, and can be hydrogen, alkyl, alkaryl or aralkyl, b is zero, and A and B can be the same or different and can be substituted (having one or more non-interfering substituents) or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable I-diketones (b=1 and x=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'—3 3'- and 4,4'-dihydroxylbenzil, furil, di-3,3'-indolylethanedione, 2,3-bornanedione (camphorquinone), biacetyl, 1,2-cyclohexanedione, 1,2-naphthaquinone, acenaphthaquinone, 1-phenyl-1,2-propanedione, and the like.

Examples of particularly preferred visible light sensitizers include the alpha-diketones: camphorquinone; glyoxal; biacetyl; 3,3,6,6-tetramethylcyclohexanedione; 3,3,7,7-tetramethyl-1,2-cycloheptanedione; 3,3,8,8-tetramethyl-1,2-cyclooctanedione; 3,3,18,18-tetramethyl-1,2-cyclooctadecanedione; dipivaloyl; benzil; furil; hydroxybenzil; 2,3-butanedione; 2,3-pentanedione; 2,3-hexanedione; 3,4-hexanedione; 2,3-heptanedione; 3,4-heptanedione; 2,3-octanedione; 4,5-octanedione; 1,2-cyclohexanedione; and 1-phenyl-1,2-propanedione. Of these, camphorquinone is the most preferred visible light sensitizer.

Examples of preferred fluorone dyes include, but are not limited to, fluorescein, 4'5'-dibromofluorescein, erythrosin B, ethyl eosin, eosin Y, and erythrosin, yellowish blend.

The molar ratio between the sensitizer and the starter includes ranges from 1.0:0.1 to 1.0:20.0, or from 1.0:0.5 to 1.0:10.0, or from 1.0:0.8 to 1.0:30. The amount of the sensitizer to be used is not particularly limited, unless the desired curing reaction cannot be achieved.

If present, the sensitizer is typically present in an amount of at least 0.1 wt.-% or at least 0.5 wt.-%.

The sensitizer can be present up to an amount of 50 or up to 35 wt.-% or up to 20 wt.-%.

Typical ranges for the sensitizer include from 0.025 wt.-% to 50 wt.-% or from 0.05 wt.-% to 40 wt.-% from 0.1 wt.-% to 25 wt.-%, wt.-% with respect to the weight of the whole composition.

If the amount of the sensitizer is too low, the desired physical properties (e.g. depth of cure) may not be obtained.

If the amount of the sensitizer is too high, the resulting composition might become too expensive from an economically point of view.

The initiator system used for hardening the composition may also comprise an electron donor compound.

Adding an electron donor compound can be beneficial, if the hardenable composition should be hardened using visible light.

A wide variety of electron donor compounds can be employed, and generally are capable of increasing the speed of polymerization and/or the depth of polymerization of the inventive composition when exposed to visible light of the desired wavelength, as compared to the same composition but excluding the electron donor compound.

Preferred electron donor compounds possess one or more (and more preferably several if not all) of the following properties:
(a) they are at least partly soluble in a polymerizable or hardenable composition;
(b) they do not absorb a significant amount of light at the wavelength of the light used to photopolymerize the composition, typically the wavelength at which the visible light sensitizer exhibits maximum absorption, by which it is meant that the electron donor compound does not detrimentally affect the performance of the visible light sensitizer;
(c) they have an oxidation potential ($E_{ox}$) greater than 0 but less than that of 1,4-dimethoxybenzene when measured versus a saturated calomel electrode (SCE);
(d) they yield a photoinitiator system that has a photoinduced potential less than that of 3-dimethylaminobenzoic acid in a standard solution of $2.9 \times 10^{-5}$ moles/g diphenyl iodonium hexafluoroantimonate and $1.5 \times 10^{-5}$ moles/g camphorquinone in 2-butanone;
(e) they impart not more than a minimal amount of objectionable colour to the polymerized resin;
(f) they can be used in a lower effective concentration than other polymerization aids. Other factors that may influence the selection of the electron donor compound for a particular composition include the cationically polymerizable resin, the iodonium salt, and the visible light sensitizer that have been chosen, as well as the shelf stability of the cationically polymerizable composition.

A wide variety of electron donor compounds can be used including biphenylene(s), anthracene(s), aromatic tertiary amine(s), aromatic ether(s), mixtures, derivatives and combinations thereof.

One class of electron donor compounds which can be used are compounds containing a biphenylene structure, including biphenylenes bearing alkyl groups.

In a preferred embodiment the alkyl groups pending on the biphenylene ring structure are arranged symmetrically.

The alkyl substituents are preferably at the positions 2, 3, 6, and 7. In a further embodiment there are not more than 2 substituents at the positions 2 and 6 or 2 and 7. Preferably, the alkyl substituents are independently selected from methyl groups or tert-butyl groups. The biphenylene structure typically does not comprise alkoxy groups like e.g. methoxy groups, being directly attached onto the biphenylene structure.

More specifically, electron donor compounds comprising the structure (VI) shown below may be employed.

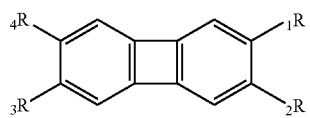

(VI)

wherein each of $R_1$ to $R_4$ is independently selected from H, or alkyl groups, wherein the R-group substituents may also cooperate to form a cycloalkyl ring. Preferred R-group substituents include methyl, ethyl, iso-propy, n-propyl, and tert-butyl groups, with the methyl and tert-butyl groups being most preferred.

More specifically, according to a preferred embodiment the electron donor compound of the invention can be characterized by at least one of the following features:
a. The biphenylene compound bears at least one, two or three but not more than four alkyl (e.g. C1 to C4) groups.
b. The substituted biphenylene compound is symmetric (reflection and/or rotation).
c. The biphenylene compound does not contain alkoxy groups directly attached onto the biphenylene structure.
d. The biphenylene compound has a molecular weight in the range of 180 to 380.

The combination of features a, c and d or b, c and d can be preferred.

Another class of electron donor compounds which can be used are compounds containing an anthracene structure.

The anthracene may be, for example, an unsubstituted anthracene or an alkyl or alkoxy substituted anthracene, such as 2-ethyl-9,10-dimethoxyanthracene (EDMOA), 2,6-di-tert-butylanthracene, 9,10-diethoxyanthracene, 1,4-dimethoxyanthracene or 9,10-dimethylanthracene. If desired, mixtures of anthracenes can be used.

In another embodiment, a combination of two or more substituted anthracenes, wherein one of the anthracenes is an alkoxy substituted anthracene (e.g., EDMOA) and the other anthracene is an alkyl, phenyl or alkoxy substituted anthracene.

It is also possible to use alone or in combination anthacenes comprising the structure (VII)

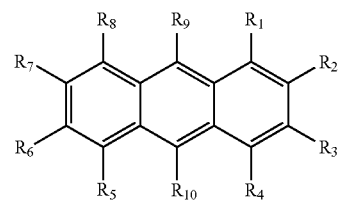

(VII)

wherein each of R1 to R10 is independently selected from H, alkyl (e.g. C1 to C10), phenyl or alkoxy groups (e.g. C1 to C10), provided that at least one of R1 to R10 is not H. Preferred R-group substituents are methyl, ethyl, propyl, butyl, tert-butyl, methoxy, and ethoxy.

Particularly useful anthracene-based compounds include: 2-ethyl-9,10-dimethoxyanthracene (EDMOA), 9,10-dimethylanthracene, 9,10-diethoxyanthracene, 1,4-dimethoxyanthracene, 9-methylanthracene, 2-ethylanthracene, 2-tert-butylanthracene, 2,6-di-tert-butylanthracene, 9,10-diphenyl-2,6-di-tert-butylanthracene, 1-amino anthracene, 2-amino anthracene and combinations thereof. All of these compounds with the exception of the 2,6-di-tert-butylanthracene derivatives are available from Sigma-Aldrich, St. Louis, Mo.

Another class of electron donor compounds which can be used are compounds containing an aromatic tertiary amine structure as e.g. described in U.S. Pat. No. 6,084,004 and/or U.S. Pat. No. 6,043,295: (which is herewith incorporated by reference):

 (VIII)

with $R^1$, $R^2$ and $R^3$ being identical or different and independently of one another selected from H, an aliphatic, aromatic or araliphatic radical having 1 to 19 or 1 to 7 carbon atoms, it being possible for one or more carbon atoms to be relaced by O, C=O, —O(C=O)—, wherein $R^1$ and $R^2$ together can from ring structures which are unsubstituted or substituted by aliphatic (C1-C19), cycloaliphatic, (C1-C20) heteroaromatic or fused aromatic radicals.

Typical examples include dimethylaniline, diethylaniline, 4-dimethylaminobenzoic acid, ethyl 4-dim ethylaminobenzoate, 3-dimethylaminobenzoic acid, 4dimethylaminobenzoin, 4-dimethylaminobenzaldehyde, and 4-dimethylaminobenzonitrile.

Another class of electron donor compounds which can be used are aryl alkyl polyether(s). Useful compounds can be characterized by the following formula:

$(R^4—O)_n\text{-Aryl-O—}CHR^3{}_2$ (IX)

with n being 1 to 3, and $R^3$ and $R^4$ being independently H or $C_{1-18}$ alkyl that is optionally substituted by one or more halogen, —CN, —OH, —SH, $C_{1-18}$ alkoxy, $C_{1-18}$ alkythio, $C_{3-18}$ cycloalkyl, aryl, substituted aryl, —COOH, COO-$HC_{1-18}$ alkyl.

Typical examples include those mentioned in U.S. Pat. No. 6,043,295 (which is herewith incorporated by reference) and in particular 1,2,4-trimethyloxybenzene.

The amount of the electron donor compound which can be used is not particularly limited, unless the desired curing reaction cannot be achieved.

If present, the electron donor compound is typically present in an amount of at least 0.025 wt.-% or at least 0.05 wt.-%.

The electron donor compound can be present up to an amount of 50 or up to 35 wt.-% or up to 20 wt.-%.

Typical ranges for the electron donor compound include from 0.025 wt.-% to 50 wt.-% or from 0.05 wt.-% to 40 wt.-% from 0.1 wt.-% to 25 wt.-%, wt.-% with respect to the weight of the whole composition.

If the amount of the electron donor compound is too low, the desired physical properties may not be obtained. If the amount of the electron donor compound is too high, the resulting composition might not yield the desired rate of polymerization.

The hardenable composition described in the present text also comprises polymeric particles as filler component (C).

The polymeric particles are composed of organic polymers, silicone elastomers or a combination or mixture thereof.

The maximum particle size of the polymeric particles is 150 μm or below, or 140 μm below.

The particle size distribution of the polymeric particles may also be characterized as follows: d50/μm=below 50 or d90/μm=below 100. D50/μm means that 50 percent of the analyzed particles have a diameter below 50 μm. D90/μm means that 90 percent of the analyzed particles have a diameter below 100 μm.

It was found that using polymeric particles having a larger particle size, in particular above 150 μm are not suitable for achieving the desired properties.

In addition the polymer particles should have a suitable hardness to allow a finely dispersion of the particles in the matrix.

Hardness often depends on a variety of properties including elasticity, viscosity, plasticity, toughness. If the hardness of the particles is too low, the particles might fibrillate during e.g. a kneading process and therefore may not improve the elastomeric matrix in the desired way. Those materials typically show a rubber like consistence. However, if the hardness of the particles is too high, there may be no significant improvement of the viscoelastic properties of the matrix.

Therefore, polymeric particles having a Shore A hardness below 70 are sometimes preferred.

The component(s) the polymeric particles are made of are typically characterized by either or more or all of the following features:

being a silicone elastomer comprising dimethylsiloxane moieties and/or being a fluoropolymer characterized by a melting point below 335° C.;

being a fluoropolymer comprising more than 99% monomer repeating units of tetra fluoro ethylene;

showing elastomeric properties like blockcopolymers of soft and hard segments e.g. like blockcopolymers of styrene, butadiene, acrylates, methycrylates or olefines.

Filler component (C) may also be characterized by at least one or more or all of the following features:

maximum particle size: 150 μm or below or 140 μm or below;

d50/μm: 50 or below; or 40 or below; or 30 or below;

d90/μm: 100 or below; or 90 or below; or 80 or below;

average particle size: 1 to 30 or 1 to 25 or 1 to 20 μm;

BET surface according to DIN ISO 9277: 1 to 20 $m^2/g$;

bulk density according to DIN EN ISO 60: below 2 $g/cm^3$ or from 0.1 to 2 $g/cm^3$;

melting peak temperature according to DIN EN ISO 12086: above 100 or above 250° C. or from above 100° C. to below 340° C.;

molecular weight: $10^4$ to $10^8$ g/mol or $10^5$ to $10^7$ g/mol;

Shore hardness A: below 70 or below 60;

polymerization type: particles obtained by emulsion or suspension polymerization or thermal degradation;

non-swellable;

shape: essentially spherical.

Suitable polymeric filler particles are those which can be combined with the other components of the hardenable composition to obtain a paste. Thus, the polymeric filler particles should not dissolve in the hardenable composition.

According to one embodiment, filler component (C) comprises fluorine containing particles having either or all of the following properties:

maximum particle size: 150 μm or below; or 140 μm or below;

Shore hardness A: 70 or below; or 65 or below;

melting peak temperature: below 340° C. or below 335° C.

This kind of filler was found to be particularly useful for the desired purpose.

Examples of filler component (C) comprising fluorine containing particles include: polytetrafluorethylene (PTFE) powder, tetrafluorethylene/hexafluorpropylene copolymer (FEP) powder, ethylene/tetrafluorethylene copolymer (ETFE) powder, tetrafluorethylene/hexafluorpropylene/vinylidenfluoride copolymer (THV) powder and mixtures thereof.

It was found that particles obtained from fully or perfluorinated polymers are sometimes more suitable than particles obtained from partially fluorinated polymers. A content of the tetra fluoro ethylene units (TFE) of the polymer forming the fluorine containing particles of above 95% or above 99% was found to be particular useful.

Using filler components comprising fluorine containing particles are sometimes preferred as the obtained composition is also sufficient storage stable, i.e. the shelf-life is not negatively affected.

Without wishing to be bound to a certain theory, it is assumed that combining cationically hardenable compounds (A) comprising at least two aziridine moieties with filler components comprising siloxane moieties may lead to a not sufficiently storage stable composition. The filler components comprising siloxane moieties often contain remaining Si—OH moieties, which may react with the aziridine moieties causing an undesirable ring-opening of these moieties.

Specific examples for fluorine containing particles include the commercially available powders:

Dyneon: TF9201Z, TF9202Z, TF9207Z, TF9205,
Dupont: Zonyl™ MP1000, MP1100, MP1200.

The dental composition described in the present text may comprise inorganic filler as component (D) or part of component (D). The inorganic filler can be comprised of one type of filler or a mixture of different types of fillers.

The nature of the inorganic filler is not particularly limited. The size of the filler particles should be such that a homogeneous mixture with the hardenable component(s) forming the resin matrix can be obtained.

The BET surface of the filler is typically in a range from 0.05 to 50 m²/g or from 0.5 to 30 m²/g or from 0.5 to 20 m²/g. Using a filler with a BET surface within this range can be beneficial to adjust the viscosity and tensile strength.

If desired, the BET surface of the filler can be determined as described in DIN 66132. Alternatively, the values for the BET surface are taken from a material data sheet provided by the supplier.

The size of the filler particles should be such that a homogeneous mixture can be obtained. The particle distribution is preferably chosen such that there are no fillers with particle sizes of more than 200 µm.

Typically, the size of the filler particles (d50 value) is below 40 µm or below 10 µm or below 5 µm. Typical ranges (d50 value) include from 0.1 to 40 µm or from 0.5 to 20 µm or from 1 to 10 µm.

The mean particle size, if desired, can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument). The term d50/µm with regard to particle size measurement means that in 50% of the analyzed volume, the particles have a size below x µm. E.g., a particle size value of below 100 µm (d50/µm) means that within the analyzed volume, 50% of the particles have a size below 100 µm.

If the filler particles are too small, the viscosity of the resulting composition might increase to a not desirable limit.

If the filler particles are too big, the detail accuracy might be negatively affected.

The filler comprises typically a filler body and a filler surface. The filler is typically in particle form.

The filler body typically comprises, consists essentially of or consists of $SiO_2$ moieties. Typical examples include quartz, cristobalite and silicates (e.g. components comprising anions of the formula $[SiO_3^{2-}]_n$ or $[Si_2O_5^{2-}]_n$) like wollastonite, nephelinsyenite, kaolin, talcum, feldspar, diatomaceous earth and mixtures and combinations thereof, wherein quartz and cristobalite are sometimes preferred.

The surface of this filler may comprise side groups with polar moieties.

By "side group" it is meant that the polar moiety is not directly attached to the filler body (e.g. like Si—OH moieties being present on the surface of a quartz filler), but that the polar moiety is linked to the surface of the filler body by a spacer group.

"Polar moieties" are defined as chemical groups having a dipole moment. Examples of such chemical groups include ethers, alcohols, thioles, phosphines, amines (prim., sec., tert.), amide, urethanes, esters, oxiranes, oxetanes, hydrated furanes, thiiranes and combinations thereof.

Side groups with polar moieties can be attached to the filler surface by applying the following steps: dispersing the filler in a solvent, adjustment of the pH, adding of a silane coupling agent, heat treatment, removal of solvent, drying of the filler, solvent exchange process, milling of the filler.

Silane coupling agents, which can be used for the surface-treatment of the filler include substances which can be characterized by formula (X):

$$E\text{-}F\text{-}G \tag{X}$$

wherein E comprises a polar moiety (as described above), F comprises Si, and G comprises at least one hydrolysable group.

By "hydrolysable group" is meant a group, which can react e.g. with OH-groups being present on the surface of the filler.

Examples of hydrolysable groups include halogens (e.g. F, Cl and Br), pseudo-halogens (e.g. azides) and alcoholates (e.g. C1-C6, alkyl and aryl).

More specifically, silane coupling agent which can be used include those which can be characterized by formula (XI)

$$A_m\text{—}B\text{—}Si(R^1)_n(OR^2)_{3-n} \tag{XI}$$

with A comprising a polar moiety (including —O—, —S—, —NH—, —OH, —SH, —CO—, —CO—O—, —CO—NH— and combinations thereof, wherein moieties comprising amines, oxiranes, and combinations thereof are preferred, B comprising a spacer group, such as (i) linear or branched C1 to C12 alkyl, (ii) C6 to C12 aryl, (iii) organic group having 2 to 20 carbon atoms bonded to one another by one or more ether, thioether, ester, thioester, thiocarbonyl, amide, urethane, carbonyl and/or sulfonyl linkages, $R^1$ comprising an alkyl group (e.g. C1 to C6) or an aryl group (e.g. C6 to C12), and $R^2$ comprising an alkyl group (e.g. C1 to C6), with m=1, 2, 3 or 4 and n=0, 1 or 2.

Non-polar moieties are e.g. —Si—OR, —Si—O—Si—, —Si—R, with R being alkyl (e.g. C1 to C6) or aryl (e.g. C1 to C6). These kinds of moieties do not show a sufficient dipole moment.

Preferably, the surface of the filler should not contain or be essentially free of acidic groups like —COOH and —$SO_3H$.

The pH value of a 10 wt.-% dispersion of the filler in water is typically within the range from 7 to 12. Using a filler having a pH value within this range can be beneficial to improve the storage stability and shelf life of the composition.

The pH value can be determined with means known to the person skilled in the art.

The following commercially available fillers were found to be particularly useful: quartz comprising amino-silane groups (e.g. Silbond™ 600 AST, Silbond™ 800 AST; Quarzwerke Frechen), wollastonite comprising amino-silane groups (e.g. Tremin™ 283-600 AST or Tremin™ 939-300 AST; Quarzwerke Frechen), quartz/kaolin mixture comprising amino-silane groups (e.g. Aktisil™ AM; Quarzwerke Frechen), quartz comprising epoxy groups (e.g. Silbond™ 600 EST, Silbond™ 800 EST; Quarzwerke Frechen) and quartz comprising trimethyl-silane groups (e.g. Silbond™ 800 RST).

Besides surface-treated fillers, non-surface treated fillers can be added. A "non-surface treated filler" in the context of the invention is a filler having a surface which has not been exposed to reactive substances resulting in a modification of the surface of the filler to make the filler more compatible with other components of the composition.

A wide variety of inorganic, hydrophilic or hydrophobic fillers may be employed such as silicas, aluminas, magnesias, titanias, inorganic salts, metallic oxides, quartz, cristobalit, kaolin, talcum, feldspar, wollastonit, nephelinsyenit, silicates and glasses. It has been found to be possible to employ mixtures of silicone dioxides, such as a diatomaceous earth and/or fumed silica. Those filler are commercially available from companies like Cabot Corporation, Wacker or Degussa under the trade names Aerosil™ (Degussa) HDK-H, HDK 2050 (Wacker), Cab-o-Sil (Cabot), Celatom MW25 (Chemag).

More specifically, fillers which can be used include calcium silicate, diatomaceous earth, zirconium silicate, montmorillonite such as bentonite, barium sulphate, calcium carbonate, plaster, glass and plastic powder.

The sizes and surface areas of the foregoing materials can be adjusted to control the viscosity and thixotropicity of the resulting compositions.

A combination of reinforcing and non-reinforcing fillers sometimes even further improves the rheology of the uncured composition and the elasticity of the cured composition.

Typical reinforcing fillers include fumed silica, carbon black and the like. They also can improve mechanical properties like tensile strength or tear strength, of the cured silicone composition.

Typical non-reinforcing fillers include precipitated silicas, diatomaceous earth, aluminas, magnesias, titanium dioxide, zirconium silicate and mixtures and combinations thereof. If present, the inorganic filler is typically present in an amount of at least 1 wt.-% or at least 5 wt.-% or at least 10 wt.-% with respect to the whole composition.

If present, the inorganic filler is typically present in an amount of at most 70 wt.-% or at most 60 wt.-% or at most 55 wt.-% with respect to the whole composition.

Thus, if present, typical ranges for the inorganic filler include from 10 to 70 or from 15 to 60 or from 20 to 55 wt.-% with respect to the whole composition.

If the amount of the filler is too low, a desired Shore hardness might not be obtained.

If the amount of the filler is too high, the elasticity of the cured composition might negatively be affected and the viscosity of the un-cured composition might be too high. Moreover, the shelf life might negatively be influenced.

According to a further embodiment, the dental composition described in the present text can also comprise one or more additives as component (E) or part of component (E). The dental compositions can contain suitable adjuvants such as accelerators, inhibitors or retarders, absorbers, stabilizers, pigments, dyes, viscosity modifiers, surfactants and wetting aids, antioxidants, and other ingredients well known to those skilled in the art.

The amounts and types of each ingredient in the composition should be adjusted to provide the desired physical and handling properties before and after polymerization. For example, the polymerization rate, polymerization stability, fluidity, compressive strength, tensile strength and durability of the dental material typically are adjusted in part by altering the types and amounts of polymerization initiator(s) and, if present, the loading and particle size distribution of filler(s). Such adjustments typically are carried out empirically based on experience with dental materials of the prior art.

Typical adjuvants include colorants like pigments, and/or dyes. Examples include titanium dioxide or zinc sulphide (lithopones), red iron oxide 3395, Bayferrox 920 Z Yellow, Neazopon Blue 807 (copper phthalocyanine-based dye) or Helio Fast Yellow ER.

Accelerators, which can be used include components having a bi- or polycyclic aromatic amine structure, especially a bi- or polycyclic aromatic tert. amine or a bi- or polycyclic aromatic like N,N-dialkyl (e.g. C1 to C12 or C1 to C6) amine. Specific examples include 1,8-bis(N,N-dimethylamino)-naphthaline and N,N-dimethyl-1-naphthylamine.

Further additives, which can be added, include stabilizers, especially free radical scavengers such as substituted and/or unsubstituted hydroxyaromatics (e.g. butylated hydroxytoluene (BHT), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethylamino)methylphenol, 4-methoxybenzylalcohol, 2,6-di-tert.-butyl-4-methylphenol ("Jonol"), 3-methoxyphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentylphenyl)-2H-benzotriazole, 2-hydroxy-4-n-octoxybenzophenone, 2-(2'-hydroxy-5'-methacryloxyethylphenyl)-2H-benzotriazole, phenothiazine, tocopherol, polyethylene imine, substituted pyridines (e.g. 2,6-di-tert.-butyl-4-methylpyridine) and HALS (hindered amine light stabilizers). Such adjuvants may optionally comprise reactive functionality so that they will be copolymerized with the resin.

All kinds of known and compatible softeners and rheology modifiers like non reactive polymeric fluids or fats commonly used in commercialized impression materials can be added Preferred are those ingredients and additives that do not add unpleasant smell or taste. Compounds that have an unpleasant smell might be removed by thinfilm evaporation, if needed.

Typical plasticisers include, e.g., compounds of the ester type such as C12- to C15-alkyl lactates, ethyl or butyl esters of citric acid or of acetylcitric acid, phthalic acid esters of relatively long, branched alcohols such as bis(2-ethylhexyl) phthalate or phthalic acid polyester, C2- to C22-dialkyl esters of C2- to C6-dicarboxylic acids such as bis(2-ethylhexyl) adipate, dioctyl maleate, diisopropyl adipate, aromatic and aliphatic sulfonic acid esters such as C2- to C20-alkylsulfonic acid esters of phenol or of C1- to C22-alkanols or typical aromatic plasticisers such as polyphenyls in a wide viscosity range, including wax-like polyphenyls such as are obtainable, for example, from the Monsanto company, isomeric mixtures of C20 to C40 aromatic compounds, with preference being given to the use of mixtures of plasticisers of the ester type and aromatic type.

Liquids such as C12-C15 alkyl acetates, liquid derivatives of citric acid, esters of phthalic acid with branched alcohols like bis(2-ethylhexyl)phthalate or polymeric phthalates, C2-C18 bis(alkyl)esters of C2-C6 dicarboxylic acids like dioctylmaleate, dioctyladipate, aromatic and aliphatic esters of sulfonic acids like Mesamoll™, aromatic and aliphatic amides of sulfonic acides like N-ethyl toluene solfonic acid amide or N-butyl benzene sulfonic acid amide, typical aromatic diluters like poly phenyls, xylyl toluene, and dixylyl toluene can be used. Also low molecular weight alcohols that may contain more than one OH-function like propane-1,2-diol may be used. From the group of polymeric compounds, polypropylene glycols and its derivatives are sometimes preferred.

An example of a preferred plasticiser combination is a mixture of acetyl tributyl citrate and dibenzyltoluene.

Suitable diluting agent(s) usually do not contain reactive moieties like —SH or —COOH, primary or secondary amino groups, but may contain —OH. Liquids such as C12-C15 alkyl acetates, liquid derivatives of citric acid, esters of phthalic acid with branched alcohols like bis(2-ethylhexyl)phthalate or polymeric phthalates, $C_2$-$C_{18}$ bis (alkyl)esters of $C_2$-$C_6$ dicarboxylic acids like dioctylmaleate, dioctyladipate, aromatic and aliphatic esters of sulfonic acids like Mesamoll™, aromatic and aliphatic amides of sulfonic acides like N-ethyl toluene solfonic acid amide or N-butyl benzene solfonic acid amide, typical aromatic diluters like poly phenyls, dibenzyl toluene, xylyl toluene, dixylyl toluene and polymeric compounds like polyethers, polyesters, polycarbonates, polytetrahydrofuranes, polyolefines can be used. Also low molecular weight alcohols that may contain more than one OH-function like propane-1,2, diol or carbonates like propylene carbonate may be used. From the group of polymeric compounds, polypropylene glycols and its derivatives are preferred.

Likewise suitable as additives are triacyl esters of glycerol of non-animal origin. Suitable additives can consist of, for example, modified fats of vegetable origin such as hydrogenated palm oil or soybean oil or synthetic fats.

Suitable fats are described in U.S. Pat. No. 6,395,801, to the full content of which reference is here made. Avocado oil, cottonseed oil, groundnut oil, cocoa butter, pumpkin seed oil, linseed oil, maize germ oil, olive oil, palm oil, rice oil, rapeseed oils, safflower oil, sesame oil, soybean oil, sunflower oil, grapeseed oil, wheat germ oil, Borneo tallow, fulwa butter, hemp oil, illlipé butter, lupin oils, candlenut oil, kapok oil, katiau fat, kenaf seed oil, kekuna oil, poppy seed oil, mowrah butter, okra oil, perilla oil, sal butter, shea butter and tung oil are especially suitable, provided that the fats in question have been hydrogenated before use. Suitable hydrogenated fats are considered to be those whose iodine value is less than 20 (measured in accordance with the DGF [German Society for Fat Science] standard C-V 11 Z2). Fat hydrogenation procedures are described, for example, in "Ullmanns Enzyklopadie der industriellen Chemie", 4th edition, volume 11, p. 469.

Mixtures of naturally occurring fats, and also synthetically prepared fats such as Softisan™ 154 or Dynasan™ 118 (from Hüls Comp.) can likewise be used. The preparation of such synthetic triacyl glycerides is relatively simple for the person skilled in the art and can be carried out by starting from glycerol and the appropriate fatty acid methyl esters. Such esterification reactions are described in, inter alia, "Houben-Weyl, Methoden der Organischen Chemie", Vol. E5/Part 1, p. 659 ff.

Preferred triacyl glycerides correspond to the formula (XII):

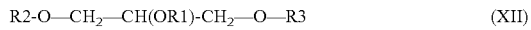

$$R2\text{-}O\text{—}CH_2\text{—}CH(OR1)\text{-}CH_2\text{—}O\text{—}R3 \quad (XII)$$

in which R1, R2 and R3 denote, each independently of the others, $C_{11}H_{23}CO$, $C_{13}H_{27}CO$, $C_{15}H_{31}CO$ or $C_{17}H_{35}CO$. Mixtures of such triacyl glycerides can also be used.

The curable composition may also include one or more surfactant(s), especially Si-containing surfactant(s) or mixture of Si-containing surfactants.

If surfactant(s) are present they are typically present in an amount sufficient and not detrimental to the desired effect or effects to be achieved.

Surfactants or hydrophilizing agents which can be employed can generally be chosen freely from all types of surfactants which improve the hydrophilicity of a polyether group containing polymer.

Preferably, the use of the surfactant should not negatively impact the material properties or curing behavior of the curable composition or at least not more than avoidable or tolerable.

Surfactant(s) can comprise an agent or a plurality of agents which are generally capable of increasing the hydrophilic character to a composition, for example as demonstrated by a decrease in the wetting angle of a drop of water or an aqueous solution or dispersion (e.g. a plaster suspension or the like) on the material (in its cured or uncured state).

In certain embodiments, the surfactant does not contain reactive groups so that it is not incorporated into the network of the hardenable composition.

Useful surfactants also include polyether carbosilanes of the general formula (XIII)

$$Q\text{-}P\text{—}(OC_nH_{2n})_x\text{—}OZ \quad (XIII)$$

in which Q stands for $R_3Si$— or $R_3Si$—$(R'$—$SiR_2)_a$—$R'$—$SiR''_2$—, where every R in the molecule can be the same or different and stands for an aliphatic C1-C18, a cycloaliphatic C6-C12 or an aromatic C6-C12 hydrocarbon radical, which can optionally be substituted by halogen atoms, R' is a C1-C14 alkylene group, R" is R in the case of a≠0 or is R or $R_3SiR'$ in the case of a=0, and a=0-2; P stands for a C2-C18 alkylene group, preferably a C2-C14 alkylene group or A—R", where A represents a C2-C18 alkylene group and R'" a functional group selected from: —NHC(O)—, —NHC(O)—$(CH_2)_{n\text{-}1}$—, —NHC(O)C(O)—, —NHC(O)$(CH_2)_v$C(O)—, —OC(O)—, —OC(O)—$(CH_2)_{n\text{-}1}$—, —OC(O)C(O)—, —OC(O)$(CH_2)_v$C(O)—, $OCH_2CH(OH)CH_2OC(O)(CH_2)_{n\text{-}1}$—, —$OCH_2CH(OH)CH_2OC(O)(CH_2)_v$C(O)— with v=1-12; Z is H or stands for a C1-C4 alkyl radical or a C1-C4 acyl radical; x stands for a number from 1 to 200 and n stands for an average number from 1 to 6, preferably 1 to 4. Thus, the element —$SiR''_2$-can also comprise the substructure —$Si(R)(R_3SiR')$—.

Other surfactants which can be used, either alone or as a mixture of two or more thereof, can be found in U.S. Pat. No. 4,657,959 (Bryan et al.), col. 4, 1. 46 to col. 6. 1. 52 as well as in EP 0 231 420 B1 (Gribi et al.; also published as AU 6,857,087) p4, 1. 1 to p. 5, 1. 16 and in the examples.

U.S. Pat. Nos. 5,750,589, 4,657,959 and EP 0 231 420 B1 are expressly described and cited herein as a source of disclosure for compounds which can be used as component (E1) according to the invention.

Some of the surfactants, which can be used can be summarized under the following formula (XIV)

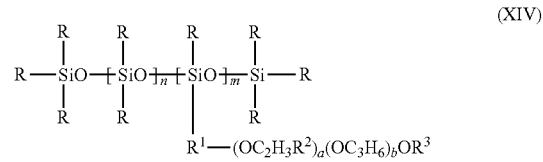

where each R is independently a monovalent hydrocarbyl radical with 1 to 22 C-atoms, $R^1$ is a divalent hydrocarbylene radical 1 to 26 C-atoms, each $R^2$ is independently hydrogen or a lower hydroxyalkyl radical, $R^3$ is hydrogen or a monovalent hydrocarbyl radical with 1 to 22 C-atoms, n and b are independently greater than or equal to zero, and m and a are independently greater than or equal to one, with the proviso that a has a sufficient value and b is small enough so that a cured composition of the invention has the desired water contact angle.

Preferably R and $R^3$ are —$CH_3$, $R^1$ is —$C_3H_6$—, $R^2$ is hydrogen, n is zero or one, m is one to five, a is five to 20 and b is 0.

Several of such ethoxylated surfactants are for example available from Momentive Performance Materials Inc. including "SILWET™" surface active copolymers. Preferred surface active copolymers include Silwet 35, Silwet L-77, Silwet L-7600 and Silwet L-7602, Silwet L-7608 and Silwet Hydrostable 68 and Silwet Hydrostable 611. Silwet L-77 is an especially preferred ethoxylated surfactant which is believed to correspond to the above formula where R and $R^3$ are —$CH_3$, $R^1$ is —$C_3H_6$—, $R^2$ is hydrogen, n is zero or one, m is one or two, a is seven, and b is 0. Also possible is the use of MASIL™ SF19, as obtainable from Lubrizol performance products, Spartanburg, US.

Examples of useful non-ionic surfactants include those according to the formula (XV):

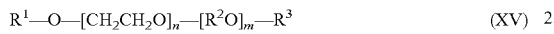

$$R^1\text{—O—}[CH_2CH_2O]_n\text{—}[R^2O]_m\text{—}R^3 \quad (XV)$$

wherein $R^1$ represents hydrogen or an aromatic or aliphatic, linear or branched hydrocarbon group having 1-20 carbon atoms, $R^2$ represents an alkylene having 3 carbon atoms, $R^3$ represents hydrogen or a C1-C3 alkyl group, n has a value of 0 to 40, m has a value of 0 to 40 and the sum of n+m being at least 2.

It will be understood that in the above formula, the units indexed by n and m may appear as blocks or they may be present in an alternating or random configuration. Examples of non-ionic surfactants according to the formula above include alkylphenol oxethylates such as ethoxylated p-isooctylphenol commercially available under the brand name TRITON™ such as for example TRITON™ X 100 wherein the number of ethoxy units is 10 or TRITON™ X 114 wherein the number of ethoxy units is 7 to 8.

Still further examples include those in which $R^1$ in the above formula represents an alkyl group of 4 to 20 carbon atoms, m is 0 and $R^3$ is hydrogen. An example thereof includes isotridecanol ethoxylated with 8 ethoxy groups and which is commercially available as GENAPOL™X080 from Clariant GmbH.

Non-ionic surfactants according to the above formula with $R^1$ and $R^3$ representing a C1-C3 alkyl chain or hydrogen and in which the hydrophilic part comprises a block-copolymer of ethoxy groups and propoxy groups may be used as well. Such non-ionic surfactants are commercially available from Clariant GmbH under the trade designation GENAPOL™ PF 40 and GENAPOL™ PF 80. Further suitable non-ionic surfactants that are commercially available include Tergitol™ TMN 6, Tergitol™ TMN 10, or Tergitol™ TMN 100X. Also statistical, alternating or block copolymers of ethylene oxide and propylene oxide are suitable surfactants according to the present invention. Such non-ionic surfactants are available e.g. under the trade name Breox™ A, Synperonic™ or Pluronic™.

The inventive composition may also comprise in addition to other ingredients and surfactants, alone or in combination an F-containing component including those described in EP application number 09162681.2, especially those described on pages 21 to 27.

There is no need for additive(s) to be present, however, if additive(s) are present, they are typically present in an amount of at least 0 wt.-% or at least 0.005 wt.-% or at least 0.01 wt.-%.

Additives can be present up to an amount of 50 wt.-% or up to 40 wt.-% or up to 35 wt.-%.

Typical ranges include from 0 wt.-% to 50 wt.-% or from 0.005 wt.-% to 40 wt.-% from 0.01 wt.-% to 35 wt.-%.

If additive(s) are present, they are typically present in an amount sufficient and not detrimental to the desired effect or effects to be achieved.

If the dental composition is to be used as dental impression material or as dental retraction material the following amounts were found to be useful:
(A) cationically hardenable compound comprising at least one aziridine moiety: from 5 to 90 wt.-% or from 10 to 80 wt.-% or from 20 to 70 wt.-%,
(B) starter: from 0.25 to 50 wt.-% or from 0.5 to 40 wt.-% or from 1 to 25 wt.-%,
(C) polymeric particles: from 2 to 70 wt.-% or from 5 to 60 wt.-% or from 10 to 50 wt.-%,
(D) inorganic filler particles: from 0 to 70 wt.-% or from 1 to 60 wt.-% or from 5 to 55 wt.-%,
(E) additive(s) or adjuvant(s): from 0 to 50 wt.-% or from 0.005 to 40 wt.-% or from 0.01 to 35 wt.-%,
wt.-% with respect to the whole composition.

As the composition is designed to be used in the medical or dental field, the composition does typically not contain components which are not desirable form a toxicological standpoint of view and may easily leak from or migrate out of the mixed composition, especially when the composition is placed into a patients' mouth.

According to one embodiment, the dental composition described in the present text does not comprise either, more or all of the following components:
silicone oil having a viscosity above 2.000.000 Pa*s at 23° C.,
salts of polyacrylic acid,
cellulose or starch powder,
fibers.

Further, the composition described in the present text does not contain polymeric particles having a particle diameter of more than 150 μm in an amount of more than 2 wt.-% or more than 1 wt.-% or more than 0.5 wt.-% with respect to the weight of the whole composition.

The invention is also directed to a process of production or manufacturing the dental composition.

Such a process typically comprises at least one mixing or compounding step of the individual component of the composition. Mixing or compounding can be accomplished by using a kneader, speedmixer or a dissolver. Typically, the filler(s) is/are added to the other components or compounds. This may facilitate the mixing procedure.

The dental composition can be obtained by combining (including mixing and kneading) the individual components or compounds of the composition, preferably under "safe light" conditions.

Suitable inert solvents may be employed if desired when formulating this mixture. Any solvent may be used which does not react appreciably with the components of the inventive compositions. Examples of suitable solvents include acetone, dichloromethane, acetonitrile, propylene carbonate, poly-THF and lactones (e.g. gamma-butyrolactone). A liquid material to be polymerized may be used as a solvent for another liquid or solid material to be polymerized. Solventless compositions can be prepared by simply dissolving the iodonium complex salt, sensitizer, and electron donor in the cationically polymerizable resin, with or without the use of mild heating to facilitate dissolution.

The individual components of the ternary photoinitiator system are provided in photopolymerizingly effective amounts (i.e., amounts effective to yield a photoinitiator system that can initiate photopolymerization of the cationically polymerizable resin or, more preferably, that can accelerate the rate of polymerization).

The dental composition described in the present text may be provided in separate parts and comprises at least a curable base paste and a catalyst or initiator paste comprising a catalyst, initiator or radiation sensitive starter suitable for curing at least part of the material of the base paste. This can be beneficial for improving the storage stability and/or shelf life.

Accordingly, the components of the composition can be included in a kit, where the contents of the composition are packaged to allow for storage of the components until they are needed.

When used, the components of the compositions can be mixed in the suitable amounts and applied using conventional techniques.

Thus, the invention also relates to a kit of parts, comprising a base paste and a catalyst paste separated from each other before use, wherein the base paste comprises the hardenable compound, and the polymeric particles and the catalyst paste comprises the starter and wherein the other optional components like the inorganic filler is/are present either in the base paste or the catalyst paste or in the base paste and the catalyst paste.

It can be preferred, if the filler(s), in particular the polymeric particles, is present in the base paste only. This may be desirable from a chemical stability point of view. If the polymeric particles are present in the base paste only, the shelf life might be improved. If the polymeric particles are present in the base paste only, they are typically present in an amount of at least 1 or at least 5 or at least 10 wt.-%, wt.-% with respect to the weight of the base paste.

Typical ranges include from 5 to 70 or from 10 to 50 or from 15 to 45, with respect to the weight of the base paste.

Providing a base paste and a catalyst paste with nearly equal viscosities may facilitate the mixing to obtain a homogeneous composition, especially if the mixing is done using a static mixing tip.

The volume ratios of catalyst paste and base paste can range from 10:1 to 1:10. Particularly preferred volume ratios of base paste to catalyst paste are from 1:1 to 10:1 or from 2:1 to 5:1 (e.g. 5 parts of base paste to 1 part of catalyst paste) or from 2:1 to 4:1.

The composition is typically stored in a container until use. Depending on the initiator system chosen, various containers can be suitable.

If the composition is provided as a one-component system, it can be stored in a container having only one chamber such as a capsule. The capsule has typically a cylindrical housing with a front and a rear end and a nozzle. The rear end of the housing is usually sealed with a movable piston. The nozzle may have a shape to allow a dispensing of the composition into the sulcus of a tooth. Typically, the dental composition is dispensed out of the capsule or container using an applier having a movable plunger (e.g. an application device having the shape of a caulk gun). Examples of suitable capsules or containers are described in U.S. Pat. No. 5,624,260, EP 1 340 472 A1, US 2007/0172789 A1, U.S. Pat. Nos. 5,893,714 and 5,865,803, the content of which with regard to the description of capsules or containers is herewith incorporated by reference.

If the composition is applied into the sulcus of a teeth (i.e. the region between gum and hard dental tissue), using a container as described in WO 2009/151983 A2 can be beneficial due to its specific geometry. Such a device can be particularly useful in a dental retraction process.

Alternatively, if the composition is provided as a two-component system, it can be stored in a dual-chamber container or cartridge and is mixed before use.

Cartridges which can be used are described e.g. in US 2007/0090079 or U.S. Pat. No. 5,918,772, the disclosure of which is incorporated by reference. Cartridges which can be used are commercially available from SulzerMixpac AG (Switzerland).

Other suitable devices can be found in WO 2005/016783 A1, WO 2007/047381, WO 2007/104037, and WO 2009/061884. If desired, the composition can also be stored in foil bags.

A further improvement of the handling properties of the composition can be seen in using an automatic mixing and metering systems for two-component compositions which have automatic conveying and mixing units, such as are described e.g. in U.S. Pat. Nos. 5,249,862, 5,286,105 and 5,419,460. The need for manual mixing of base pastes and catalyst pastes, above all when mixing larger quantities of material, can be eliminated, since this can take place automatically and within a short period of time. The result is usually a homogeneous product which is essentially free of air bubbles. Commercially available devices are distributed by 3M ESPE under the brand Pentamix™ or Pentamix™ 2 or Pentamix™ 3.

The disclosure of the above mentioned patents is herewith explicitly mentioned and regarded as part of the text of this invention and herewith incorporated by reference.

In practice, the composition (if provided as a two-component system) can be syringed through a static or dynamic mixing device onto a surface or into an impression tray or onto the patients' teeth or tissue (including sulcus) and placed in the patients' mouth. The mixed pastes may also be applied using an applicator like an elastomer syringe.

If the dental composition contains a radiation sensitive starter, the radiation which can be used for starting the hardening reaction of the radiation curable inventive composition is not particularly limited. All kind of radiation can be used, which is sufficient in energy. The more energetic the radiation is, the less time is typically required to start the hardening reaction.

Radiation having a wavelength in the range from 250 to 1,000 nm or from 350 to 700 nm or from 400 to 500 nm was found to be useful.

In the dental and orthodontic area commercially polymerization lamps are sold under the trade name Elipar™ Freelight (3M ESPE).

If desired the composition can be cured at ambient temperature or a temperature which is typically present in the mouth of a patient (e.g. within a range from 15 to 40° C.) at ambient pressure (e.g. within a range from 850 to 1,100 hPa).

Depending on the thickness and transparency of the composition to be cured, radiation is typically applied for a time period ranging from a few seconds to a few minutes, e.g. from 1 s to 120 s or from 5 s to 60 s from 10 s to 40 s.

The following combination of parameters was found to be particularly effective:

Wavelength: from 400 to 500 nm.
Duration: from 2 s to 2 min or from 10 s to 1 min or from 20 s to 40 s.
Power: from 300 mW/cm$^2$ to 2500 mW/cm$^2$'

The exposure of the composition to radiation can be repeated, if desired.

The dental composition can be used as dental impression material or for the production of crowns and/or bridges, including temporary or long term crowns and bridges. In the latter case, the composition is used as a mould to be filled with the (temporary or long term) crown and/or bridge material, which is typically based on polymerizable (meth) acrylates or similar chemical reactants.

The dental composition is especially useful for producing dental materials like precision impression materials, bite registration materials, duplicating materials, modelling materials, situation impression materials.

The composition can be used e.g. for making impressions of soft and hard dental tissue. This can be achieved simply, e.g. filling the material into a dental tray and putting the tray into the mouth of a patient.

In this respect the invention is directed to a process of taking an impression of the dental situation in the mouth of a patient, the process comprising the steps of
providing the hardenable composition as described in the present text,
bringing the hardenable composition in contact with the surface of the dental situation in the mouth of a patient,
letting the hardenable composition cure,
removing the hardened composition from the mouth of the patient.

According to a further embodiment, the dental composition can be used as or for producing a dental retraction material.

Due to the presence of polymeric particles as filler component in the hardenable composition, the viscosity and consistency of the obtained composition is such that the hardenable composition can not only be easily placed in the sulcus of a tooth, but also exerts sufficient pressure on the surrounding soft tissue having the result that the sulcus is widened. Due to its elastomeric properties in its cured stage, the composition can also be easily removed from the sulcus after hardening.

Thus, the curable dental composition described in the present text is not only suitable as dental impression material but also as dental retraction material.

If used in the dental field, curing is preferably carried out at a temperature below 50° C. and preferably below 40° C. A typical time for cure of curable compositions as described in the present text used for dental impressioning is within 20 min, or preferably within 10 min, after mixing the components of the composition. For dental duplicating applications or dental modelling applications that take place in the professional dental laboratory, cure times of up to 45 min is generally acceptable. In other applications (e.g., sealing, moulding, coating, adhesively fixing), other cure times may be typical and higher cure temperatures may be acceptable. Nevertheless, setting times in the range of 30 min or 1 hour can still be useful.

The material is generally regarded as cured, if the cured material fulfils the requirements for its use. For example, a dental precision impression material typically fulfils the requirements for its use when it fulfils the requirements of ISO 4823:2000 (such as compatibility with gypsum, strain in compression, recovery from deformation, detail reproduction, linear dimensional change).

According to another aspect, the invention is directed to kit of parts comprising a composition A and a composition B. Composition A and composition B differ from each other at least with respect to one property. Differentiating properties include consistency (e.g. determined according to ISO 4823), viscosity, transparency and/or curing mechanism.

A difference in consistency or transparency might e.g. be caused by a different filler content or a different content of hardenable components present in the composition. Composition A is typically also a hardenable composition and can contain essentially the same components as composition B. Composition B is the composition as it is described in the present text.

A difference in the curing mechanism can be achieved, e.g. if composition B contains a radiation sensitive starter and composition A contains a tri alkyl sulfonium initiator.

Such a kit might be useful in a process comprising the steps of
a) providing a composition A having the property A and a composition B having the property B, property A and property B being different from each other (e.g. with respect to curing mechanism),
b) bringing composition B into contact with a surface,
c) applying radiation to composition B,
d) bringing composition A into contact with composition B,
e) removing composition A and composition B from the surface.

Such a process can be beneficial if applied in the dental field.

Composition B can be applied e.g. to the surface of an individual tooth or several teeth. The hardening of composition B can be initiated by applying radiation. If desired, thereafter composition A can be applied and brought in contact with at least the surface of composition B.

Composition B is typically also a curable composition, but the curing reaction might be initiated by a different mechanism, i.e. not initiated by radiation. Such curing mechanisms include addition, condensation (e.g. of VPS materials) and ring-opening curing mechanisms (e.g. ring-opening of aziridines).

According to one embodiment composition A may comprise a cationically hardenable compound comprising at least one aziridine moiety and a sulfonium initiator being different from the radiation sensitive starter. Suitable sulfonium initiators for this embodiment include those described in formula I of US 2008/200585 and formula I of U.S. Pat. No. 4,167,618.

As composition A and composition B are in close contact, they typically adhere to each other during the hardening reaction. This may facilitate the removal of both, the hardened composition A and the hardened composition B in one step and may also help saving time and reducing stress for the practitioner e.g. when taking an impression of the dental hard and soft tissue of a patient.

Previously, the practitioner had to adjust the individual steps and often had not enough time for applying the impression material precisely to the tooth. The hardening reaction typically started immediately upon mixing the catalyst and base paste needed for producing the curable composition.

The composition described in the present text and the method of its possible application may help to facilitate the former process, which is sometimes referred to as putty/wash or one-step technique in the dental field.

Thus, composition B—as described above—is typically used for making impressions of individual tooth, teeth or of the sulcus of the tooth or teeth, whereas composition A is used for recording the geometric relationship of the individual impressions achieved by curing composition B.

A further embodiment of the invention is directed to a process comprising the steps of:
- providing the curable dental composition as described in any of the preceding claims,
- applying one portion of the dental composition to a surface, the surface being either the sulcus, the gum, the hard dental tissue of a patient or all of these surfaces,
- letting the composition harden,
- applying a further portion of the curable dental composition as described in any of the preceding claims on top of the surface of the hardened composition
- letting the composition harden,
- removing the combined hardened compositions from the surface.

Such a process can also be useful for combining dental retraction and dental impressioning.

In a first step, the hardenable composition is placed into the sulcus of one or more teeth.

In a second step, the hardenable composition is hardened either due to a starter being already present in the composition or due to a starter which is generated after applying radiation.

The hardened composition will exert pressure on the surrounding tissue, thus affecting a retraction.

In a further step, the hardenable composition is applied again, this time, at least on top of the surface of the hardened composition.

As the chemical nature of the composition is identical, both material will adhere together and the combined hardened compositions can be removed easily.

If desired, removal of the compositions can also be effected by using a dental impression tray filled with another dental impression material.

The further dental impression material contained in the dental impression tray is put on top of the surface of the second portion of the curable dental composition described in the present text.

Finally, the dental impression tray is removed from the mouth of the patient, the dental impression tray containing the following compositions: two parts of the hardened dental composition described in the present text and one part of the further dental impression material.

Features and advantages of this invention are further illustrated by the following examples, which are in no way intended to be limiting thereof. The particular materials and amounts thereof recited in these examples, as well as other conditions and details, should not be construed to unduly limit this invention.

Examples

Unless otherwise indicated, all parts and percentages are on a weight basis, all water is de-ionized water and all molecular weights are weight average molecular weight. Moreover, unless otherwise indicated all experiments were conducted at ambient conditions (23° C.; 1013 mbar).

General Procedures:

Mixing was typically done using a speedmixer (Speed-Mixer DAC 150 FVZ, Hauschild Engineering) with a speed of 2400 rounds per minute until a homogeneous paste was obtained (typically within 2 to 4 min). The pastes in Table 4 were kneaded in a 3-finger vacuum kneader for 40 minutes.

Photopolymerization was initiated using an Elipar™ S10 dental photocuring source (3M ESPE). The source emitted radiation predominantly in the range of 430-480 nm and had a light intensity of about 1200 mW/cm$^2$.

Description of Measurements

Shore Hardness A

The Shore hardness A was determined according to DIN 53505:2000-08 using a "Härteprüfgerät Zwick 3100/Prüfeinrichtung 7206" (Zwick GmbH &Co. Ulm) as the measuring device.

Viscosity

If desired, the viscosity can be measured at 23° C. using a Haake Rotovisco 1 device with a plate/plate system (diameter 20 mm) and a slit of 0.2 mm. The viscosity values (Pas) and share stress values (Pa) can be recorded for each share rate (starting from 10 l/s to 110 l/s in 10 l/s steps. For each share rate, a delay of 5 seconds was used before collecting data. The above mentioned method of measurement corresponds essentially to DIN 53018-1.

Tensile Strength and Elongation at Break

If desired, the tensile strength and elongation at break of the compositions can be determined according to DIN 53504:2009:10.

Elastic Recovery

If desired, Elastic Recovery of the compositions can be determined according to ISO 4823:2000-12.

Maximum Particle Size and Particle Size Distribution

The maximum particle size can be determined by laser diffraction using a Cilas 1064 Granulometer in "Dry Mode". Results are calculated using the Fraunhofer approximation without Mie correction.

Consistency

Consistency of the composition was determined according to ISO 4823:2007-10.

Brightness

The brightness was determined as follows: Cured samples of the material to be analysed were measured in a spectral photometer (Colour i7, X-Rite) using the reflection method. The sample which is next to a so called Ulbricht sphere will be irradiated by a diffuse light beam and observed by an angle of 8°. The outcome of the reflected light will be calculated by the CIE-method, well known to a person skilled in the art. The figures itself can be specified by using the L*a*b*values. The L* value is an indicator of brightness. A white sample has the L* value 100. The higher the L* value, the brighter the sample is.

Swellability

If desired, the swellability can be determined as follows: 5 g material or particles are dispersed in 50 ml water (23° C.) and stirred for 5 min. The suspension is filtrated. The material or particles are put in water and the volume expansion of the material or particles determined with the Archimedes method (i.e. by displacement of water).

Scannability

The scannability was determined as follows: Cured samples of the material to be analysed were scanned in a red-light impression scanner (iSeries; Dentalwings). STL (surface tessellation language) files created by the scanner define the surface of 3D objects as triangles. The STL files obtained were analysed with a suitable 3D software (e.g. 3D-Tool-FreeViewer). The ratio of the number triangles in the STL file and the surface of the impression scan was calculated. The data was analysed by 1-way ANOVA with general linear model and pairwise comparison using the Tukey test ($p<0.05$)—(see also Abstract #1362, AADR 2012).

ABBREVIATIONS

TABLE 1

| Component | Availability (e.g.) | Description |
|---|---|---|
| Impregum ™ Soft (IS) | 3M ESPE | Polyether dental impression material |
| TF9207Z | Dyneon | Fluorpolymer particles; max. particle size: 46 μm |
| TF9205 | Dyneon | Fluorpolymer particles; max. particle size: 46 μm |
| TF1750 | Dyneon | Fluorpolymer particles; max. particle size: 110 μm |
| FEP6322AZ | Dyneon, milled and sieved (50 μm) | Fluorpolymer particles; max. particle size: 56 μm |
| PFA6503PAZ | Dyneon | Fluorpolymer particles; max. particle size: 110 μm |
| $TiO_2$ | SigmaAldrich | Titanium dioxide |
| polyether surfactant | Momentive | Silwet ™ L-77 |
| fluorinated polyether | | as described in EP 2 072 029 B1, Example 1 |
| polyalkylen oxide diacetate | | Mn: about 6,000 g/mol |
| fat (trisacylic ester of glycerine) | | |
| difunctional aziridino polyether | | Mn: about 6,000 (from EO (ethylene oxide) I THF (tetrahydrofurane); obtainable as described in DE 1 745 810 A1 |
| dibenzyl toluene | SigmaAldrich | CAS-No 26898-17-9 |
| p-toluene sulfonic acid | SigmaAldrich | |
| EO/PO copolymer (CAS-No. 9038-95-3) | Bayer MaterialScience | Polyether polyol |

Analysis of Scannability

For analysing the influence of polymeric fillers on scannability, the following tests were conducted.

General Description

In a series of examples the product Impregum™ Soft (Impregum™ Soft Tray Impression Material in Garant Cartridge Delivery, volume base:catalyst v/v=2:1, Refill package, order number 31785, base paste batch #529179, catalyst paste batch #510417; 3M ESPE) was combined with different polymeric fillers.

The polymeric fillers were added to the base paste of Impregum™ Soft such that 10 wt.-% of each filler were mixed into 100 g of base paste. The resulting material was mixed with Impregum™ Soft catalyst paste using a v:v=2:1 Garant cartridge and a static mixing tip. The mixtures were analysed and the following data was recorded (Table 2):

TABLE 2

| base paste | consistency [mm] | setting begin [min] | setting, end [min] | Shore A (RT/24 h) | tensile strength [MPa] | elongation at break [%] | elastic recovery [%] | brightness L*-value | scannability |
|---|---|---|---|---|---|---|---|---|---|
| IS | 36.0 | 2.07 | 4.20 | 59 | 2.52 ± 0.14 | 347 ± 36 | 98.9 | 38.1 | 36.1 |
| 100 IS + 10 TF 9207 Z | 34.5 | 2.19 | 4.55 | 61 | 2.62 ± 0.14 | 381 ± 12 | 98.7 | 39.5 | 31.4 |
| 100 IS + 10 TF 9205 | 34.0 | 2.27 | 4.35 | 60 | 2.27 ± 0.14 | 335 ± 31 | — | 39.3 | 30.2 |
| 100 IS + 10 FEP 6322 AZ | 34.5 | 2.21 | 4.29 | 59 | 2.32 ± 0.12 | 314 ± 15 | — | 38.9 | 32.0 |
| 100 IS + 10 PFA 6503 PAZ | 34.5 | 2.24 | 4.34 | 59 | 2.37 ± 0.14 | 343 ± 29 | — | 38.8 | 32.8 |
| 100 IS + 1.0 TiO2 | 36.0 | 2.24 | 4.29 | 60 | 2.42 ± 0.23 | 332 ± 55 | — | 51.1 | 29.5 |

The data shows that there is a thickening effect with no or only very small effect on Shore hardness but with an improvement of scannability without the effect of making the colour pale as it is observed if $TiO_2$ was used.

Analysis of Shore Hardness and Consistency

For analysing the influence of polymeric fillers on Shore hardness and consistency, the following tests were conducted:

General Description

Polyether impression materials were manufactured under vacuum using a three finger kneader. In this series of experiments the type of filler was varied. The amount of filler used was adapted to obtain the same consistency of the pastes.

Formulation (Table 3):

TABLE 3

| | Content [g] |
|---|---|
| Base paste A | |
| difunctional aziridino polyether Mn: 6000 (from EO (ethylene oxide) I THF (tetrahydro furane) | 58.50 |
| fat (trisacylic ester of glycerine) | 13.47 |
| dibenzyl toluene (CAS-No 26898-17-9) | 5.85 |
| pigment(s) | 2.00 |
| polyether surfactant | 3.50 |
| fluorinated polyether | 2.00 |
| polyalkylene oxide diacetate (Mn about 6,000 g/mol) | 0.50 |
| flavours, fragrances | 0.18 |
| Catalyst paste A | |
| EO/PO copolymer (CAS-No. 9038-95-3) | 57.70 |
| hydrophobic precipitated silica (CAS-No. 67762-90-7, 90 m²/g) | 11.00 |
| demineralized water | 5.00 |
| p-toluene sulfonic acid monohydrate | 4.00 |
| pigment(s) | 0.30 |

Base and Catalyst Pastes were mixed in a 2:1 (Base:Catalyst) weight ratio.

The mixtures were analysed and the following data was recorded (Table 4):

TABLE 4

| Example | Filler | consistency [mm] | Shore Hardness A (24 h) |
|---|---|---|---|
| 86 g Base Paste A + 14.00 g Filler 78 g Catalyst Paste A + 22.00 g Filler | Diatomaceous earth | 33 | 52 |

TABLE 4-continued

| Example | Filler | consistency [mm] | Shore Hardness A (24 h) |
|---|---|---|---|
| 86 g Base Paste A + 14.00 g Filler 78 g Catalyst Paste A + 22.00 g Filler | TF 9207Z | 34 | 41 |
| 86 g Base Paste A + 14.00 g Filler 78 g Catalyst Paste A + 22.00 g Filler | PVDF | 34 | 45 |
| 86 g Base Paste A + 40.00 g Filler 78 g Catalyst Paste A + 32.00 g Filler | PFA | 33.5 | 40 |

The data shows that by using the polymeric filler particles described in the present text, the Shore hardness of the set material can be decreased, while maintaining the consistency.

The invention claimed is:

1. A curable dental composition comprising:
a cationically hardenable compound (A) comprising at least two aziridine moieties,
a starter (B) being suitable to cure the hardenable compound (A),
polymeric particles as filler component (C),
the polymeric particles having a maximum particle size of 150 μm or below and
the component(s) the polymeric particles are made of being based on fluoropolymers comprising more than 99% monomer repeating units of tetra fluoro ethylene.

2. The composition of claim 1, filler component (C) being characterized by at least or all of the following parameters:
maximum particle size: 150 μm or below;
d50/μm: 50 or below;
d90/μm: 100 or below;
average particle size: 1 to 30 μm;
BET surface according to DIN ISO 9277: 1 to 20 m$^2$/g;
bulk density according to DIN EN ISO 60: below 2 g/cm$^3$ or from 0.1 to 2 g/cm$^3$;
melting peak temperature according to DIN EN ISO 12086: above 100° C.;
Shore hardness A: below 70;
molecular weight: $10^4$ to $10^8$ g/mol;
polymerization type: particles obtained by emulsion or suspension polymerization or thermal degradation,
non-swellable.

3. The composition of claim 1, comprising in addition an inorganic filler (D), the inorganic filler being characterized by the following feature: BET surface: from 50 to 400 m$^2$/g.

4. The composition of claim 1, the starter being selected from Lewis acids or Broensted acids or precursors of Lewis acids which can be activated by radiation to produce a Lewis acid.

5. The composition of claim 1, the cationically hardenable compound (A) comprising a backbone containing moieties selected from polyether, polyesters, polyamides, polyurethanes, silicones and combinations thereof.

6. The composition of claim 1, the aziridine moiety of compound (A) being characterized by the following formula

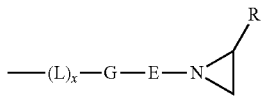

wherein
R represents H, C1-C12 alkyl, C2-C12 alkenyl, C2-C12 alkinyl, C7-C15 alkylaryl, C7-C15 arylalkyl or C3-C12 cycloalkyl, and wherein hydrogen atoms can be replaced by Cl or F and/or wherein up to 5 carbon atoms may be replaced by atoms or group of atoms selected from O, CO, N or S,
E represents a C1-C18 branched or unbranched hydrocarbon chain wherein up to 5 carbon atoms can be replaced by atoms or group of atoms selected from O, CO, N or S, G represents a group selected from C(O)O, C(O)NR, C(O), C(O)C(O), C(O)(CH$_2$)$_m$C(O) with m=1 to 10, C(S)NR or CH$_2$,
L represents O, S or NR, with x=0 or 1.

7. The composition of claim 1, filler component (C) being present in an amount from 2 to 70 wt.-% with respect to the weight of the whole composition.

8. The composition of claim 3, comprising the individual components in the following amounts:
cationically hardenable compound (A) comprising at least two aziridine moieties: from 5 to 90 wt.-%,
starter (B): from 0.25 to 50 wt.-%,
polymeric particles (C): from 2 to 70 wt.-%,
inorganic filler (D): from 1 to 80 wt.-%,
wt.-% with respect to the weight of the whole composition.

9. The composition of claim 1, being characterized by at least one or all of the following parameters after hardening:
L* value: below 50%;
Tensile strength according to DIN 53504: at least 1.2 MPa;
Elongation at break according to DIN 53504: at least 100%;
Recovery from deformation according to ISO 4823: at least 90%;
Shore A hardness according to DIN 53505 after 24 h: below 70.

10. The composition of claim 3, comprising:
the cationically hardenable compound (A) comprising at least two aziridine moieties and being present in an amount from 20 to 70 wt.-%,
the starter (B) being a Lewis or Broensted acid or precursor of a Lewis acid and being present in an amount from 1 to 25 wt.-%,
the polymeric particles (C) in an amount from 2 to 60 wt.-%,
inorganic filler (D) containing SiO2 particles in an amount from 5 to 50 wt.-%,
wt.-% with respect to the weight of the whole composition,
the polymeric particles having a maximum particle size of 150 μm or below and being composed of fluoropolymers comprising more than 99% monomer repeating units of tetra fluoro ethylene.

11. A kit of parts for preparing an elastomeric composition comprising
Part I and Part II,
Part I comprising a cationically hardenable compound (A) and polymeric particles (C),
Part II comprising a starter (B),
wherein inorganic filler (D) are either present in Part I or Part II or Part I and Part II, wherein the compound (A), the starter (B), the polymeric particles (C) and the inorganic filler (D) are of claim 3.

12. A method of using the composition of claim 1 or the kit of parts according to claim 11 for producing a dental impression material or a dental retraction material.

13. The composition of claim 1, wherein the scannability is enhanced, the hardness is reduced, or a combination thereof when in its hardened state.

* * * * *

UNITED STATES PATENT AND TRADEMARK OFFICE
CERTIFICATE OF CORRECTION

PATENT NO. : 10,751,262 B2
APPLICATION NO. : 15/533293
DATED : August 25, 2020
INVENTOR(S) : Andreas Maurer et al.

It is certified that error appears in the above-identified patent and that said Letters Patent is hereby corrected as shown below:

In the Specification

Column 1
Line 48, delete "Impregum™" and insert -- Impregum™, --, therefor.
Line 49, delete "hydrosilation" and insert -- hydrosilylation --, therefor.
Line 52, delete "hydrosilation" and insert -- hydrosilylation --, therefor.

Column 2
Line 51, delete "scannned." and insert -- scanned. --, therefor.

Column 7
Line 39, delete "SulzerMixpac" and insert -- Sulzer Mixpac --, therefor.

Column 8
Lines 3-4, delete "wettabilty" and insert -- wettability --, therefor.

Column 10
Lines 39-40, delete "tetrahydrofurane" and insert -- tetrahydrofuran --, therefor.
Line 40, delete "epichlorohydrine" and insert -- epichlorohydrin --, therefor.
Line 55, delete "tetrahydrofurane." and insert -- tetrahydrofuran. --, therefor.

Column 11
Line 16, delete "azirdine" and insert -- aziridine --, therefor.
Line 33, delete "sub stituents" and insert -- substituents --, therefor.

Column 12
Line 47, delete "0," and insert -- O, --, therefor.

Column 13
Line 42, delete "phenol sulphonic" and insert -- phenolsulphonic --, therefor.

Signed and Sealed this
Seventeenth Day of November, 2020

Andrei Iancu
*Director of the United States Patent and Trademark Office*

Column 15
Line 30, delete "Arl" and insert -- Ar1 --, therefor.

Column 16
Line 62, delete "hexafluoroantimonat," and insert -- hexafluoroantimonate, --, therefor.
Line 63, delete "tetrafluorborat." and insert -- tetrafluoroborate. --, therefor.

Column 17
Line 25, delete "sensitzer" and insert -- sensitizer --, therefor.

Column 18
Line 20, delete "dihydroxylbenzil," and insert -- dihydroxybenzyl --, therefor.
Line 22, delete "naphthaquinone," and insert -- naphthoquinone, --, therefor.
Lines 22-23, delete "acenaphthaquinone," and insert -- acenaphthoquinone, --, therefor.
Line 29, delete "hydroxybenzil;" and insert -- hydroxybenzyl; --, therefor.

Column 19
Line 60, delete "iso-propy," and insert -- iso-propyl, --, therefor.

Column 20
Line 24, delete "anthacenes" and insert -- anthracene --, therefor.
Line 61, delete "relaced" and insert -- replaced --, therefor.
Line 67, delete "4-dim ethylaminobenzoate," and insert -- 4-dimethylaminobenzoate, --, therefor.

Column 21
Lines 1-2, delete "4dimethylaminobenzoin," and insert -- 4-dimethylaminobenzoic, --, therefor.
Line 12, delete "alkythio," and insert -- alkylthio, --, therefor.

Column 22
Line 6, delete "blockcopolymers" and insert -- block copolymers --, therefor.
Line 7, delete "blockcopolymers" and insert -- block copolymers --, therefor.
Line 44, delete "polytetrafluorethylene" and insert -- polytetrafluoroethylene --, therefor.
Line 45, delete "tetrafluorethylene/hexafluorpropylene" and insert
-- tetrafluoroethylene/hexafluoropropylene --, therefor.
Line 46, delete "tetrafluorethylene" and insert -- tetrafluoroethylene --, therefor.
Lines 47-48, delete "tetrafluorethylene/hexafluorpropylene/vinylidenfluoride" and insert
-- tetrafluoroethylene/hexafluoropropylene/vinylidenefluoride --, therefor.

Column 23
Line 50, delete "nephelinsyenite," and insert -- nepheline syenite, --, therefor.

Column 25
Lines 3-4, delete "cristobalit," and insert -- cristobalite, --, therefor.
Line 4, delete "wollastonit," and insert -- wollastonite, --, therefor.
Line 4, delete "nephelinsyenit," and insert -- nepheline syenite, --, therefor.

Column 26
Line 9, delete "naphthaline" and insert -- naphthalene --, therefor.
Line 34, delete "added" and insert -- added. --, therefor.
Line 37, delete "thinfilm" and insert -- thin film --, therefor.
Line 60, delete "acides" and insert -- acids --, therefor.
Line 60, delete "solfonic" and insert -- sulfonic --, therefor.

Column 27
Line 13, delete "acides" and insert -- acids --, therefor.
Line 13, delete "solfonic" and insert -- sulfonic --, therefor.
Line 14, delete "solfonic" and insert -- sulfonic --, therefor.
Lines 17-18, delete "polytetrahydrofuranes," and insert -- polytetrahydrofurans, --, therefor.

Column 28
Line 32, delete "A—R″," and insert -- A—R‴ --, therefor.
Line 36, delete "$OCH_2CH(OH)CH_2OC(O)$" and insert -- $—OCH_2CH(OH)CH_2OC(O)$ --, therefor.

Column 31
Line 4, delete "photopolymerizingly" and insert -- photopolymerzingly --, therefor.

Column 32
Line 12, delete "SulzerMixpac" and insert -- Sulzer Mixpac --, therefor.
Line 65, delete "$mW/cm^2$"" and insert -- $mW/cm^2$. --, therefor.

Column 35
Line 11, delete "composition" and insert -- composition, --, therefor.

Column 37
Line 8, delete "Fluorpolymer" and insert -- Fluoropolymer --, therefor.
Line 10, delete "Fluorpolymer" and insert -- Fluoropolymer --, therefor.
Line 12, delete "Fluorpolymer" and insert -- Fluoropolymer --, therefor.
Line 14, delete "Fluorpolymer" and insert -- Fluoropolymer --, therefor.
Line 15, delete "Fluorpolymer" and insert -- Fluoropolymer --, therefor.
Line 21, delete "polyalkylen" and insert -- polyalkylene --, therefor.
Line 23, delete "(trisacylic" and insert -- (tricyclic --, therefor.
Line 26, delete "(tetrahydrofurane);" and insert -- (tetrahydrofuran); --, therefor.
Line 31, delete "MaterialScience" and insert -- Material Science --, therefor.

Column 38
Line 22, delete "(tetrahydro furane)" and insert -- (tetrahydro furan) --, therefor.
Line 23, delete "(trisacylic" and insert -- (tricyclic --, therefor.

In the Claims

Column 40
Line 3, delete "alkinyl" and insert -- alkynyl --, therefor.